(12) United States Patent
Alizadeh et al.

(10) Patent No.: US 9,605,320 B2
(45) Date of Patent: Mar. 28, 2017

(54) METHOD OF PREDICTING RESPONSIVENESS OF B CELL LINEAGE MALIGNANCIES TO ACTIVE IMMUNOTHERAPY

(75) Inventors: Arash Ash Alizadeh, San Mateo, CA (US); Dan Denney, Fremont, CA (US); Ronald Levy, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 261 days.

(21) Appl. No.: 13/978,360

(22) PCT Filed: Jan. 10, 2012

(86) PCT No.: PCT/US2012/020802
§ 371 (c)(1),
(2), (4) Date: Sep. 19, 2013

(87) PCT Pub. No.: WO2012/096975
PCT Pub. Date: Jul. 19, 2012

(65) Prior Publication Data
US 2014/0220562 A1 Aug. 7, 2014

Related U.S. Application Data

(60) Provisional application No. 61/461,211, filed on Jan. 13, 2011.

(51) Int. Cl.
| | | |
|---|---|---|
| C12Q 1/68 | (2006.01) | |
| G01N 33/574 | (2006.01) | |
| G01N 33/68 | (2006.01) | |

(52) U.S. Cl.
CPC ..... *C12Q 1/6886* (2013.01); *G01N 33/57426* (2013.01); *G01N 33/686* (2013.01); *C12Q 2600/106* (2013.01); *C12Q 2600/156* (2013.01); *G01N 2800/52* (2013.01)

(58) Field of Classification Search
None
See application file for complete search history.

(56) References Cited

U.S. PATENT DOCUMENTS

| | | |
|---|---|---|
| 6,455,043 B1 | 9/2002 | Grillo-Lopez |
| 7,589,181 B2 | 9/2009 | Kashmiri et al. |
| 2005/0048071 A1 | 3/2005 | Bae |
| 2007/0004909 A1 | 1/2007 | Johnson et al. |
| 2010/0215651 A1* | 8/2010 | Blein et al. ................ 424/133.1 |

FOREIGN PATENT DOCUMENTS

| | | |
|---|---|---|
| WO | WO9408601 | 4/1994 |
| WO | WO2012096975 | 7/2012 |

OTHER PUBLICATIONS

Al et al., "Anti-idiotype antibody response after vaccination correlates with better overall survival in follicular lymphoma", Blood (2009), 113:5743-5746.
Bendandi et al., "Hybridoma-Derived Idiotype Vaccine for Lymphoma: Approval Must Wait", Pharmaceuticals (2010), 3:667-678.
Jurcic et al., "General Principles of Tumor Immunotherapy: Monoclonal Antibody Therapy of Cancer", Springer (2007), Chapter 14, pp. 321-342.
Nikula et al., "Impact of the high tyrosine fraction in complementarity determining regions: measured and predicted effects of radioiodination on IgG immunoreactivity", Mol Immunol (1995), 32(12):865-872.
Stern et al., "Cancer Vaccines and Immunotherapy", Cambridge University Press (2000), Cambridge, United Kingdom.
Volpe et al., "Large-scale analysis of human heavy chain V(D)J recombination patterns", Immunome Research (2008), 4:3.
Vuist et al., "Lymphoma Regression Induced by Monoclonal Anti-Idiotypic Antibodies Correlates With Their Ability to Induce Ig Signal Transduction and is Not Prevented by Tumor Expressiono f High Levelso f Bcl-2 Protein", Blood (1994), 83(4):899-906.
Weng et al., "Clinical Outcome of Lymphoma Patients After Idiotype Vaccination is Correlated With Humoral Immune Response and Immunoglobulin G Fc Receptor Genotype", J Clin Oncol (2004), 22(23):4717-4724.
Xiang et al., "Light-chain framework region residue Tyr71 of chimeric B72.3 antibody plays an important role in influencing the TAG72 antigen binding", Protein Engineering (1999), 12(5):417-421.

\* cited by examiner

*Primary Examiner* — Jehanne Sitton
(74) *Attorney, Agent, or Firm* — Pamela J. Sherwood; Bozicevic, Field & Francis LLP

(57) ABSTRACT

Predictive biomarkers identify those patients suffering from immunoglobulin positive ($Ig^+$) B lineage malignancies that are responsive to active immunotherapy, where the active immunotherapy comprises vaccination with a tumor-specific idiotype-immunogen. It is shown herein that patient responsiveness to the idiotype-immunogen is dependent upon the sequence of the immunogen, where an immunogen having a low number of tyrosine residues in the CDR1 (herein termed $CDR1-Y^{lo}$) regions of one or both of the immunogen heavy and light chains is predictive of a positive anti-tumor response, while a high number of CDR1 tyrosine residues (herein termed $CDR1-Y^{hi}$) is predictive of a low anti tumor response.

4 Claims, 14 Drawing Sheets

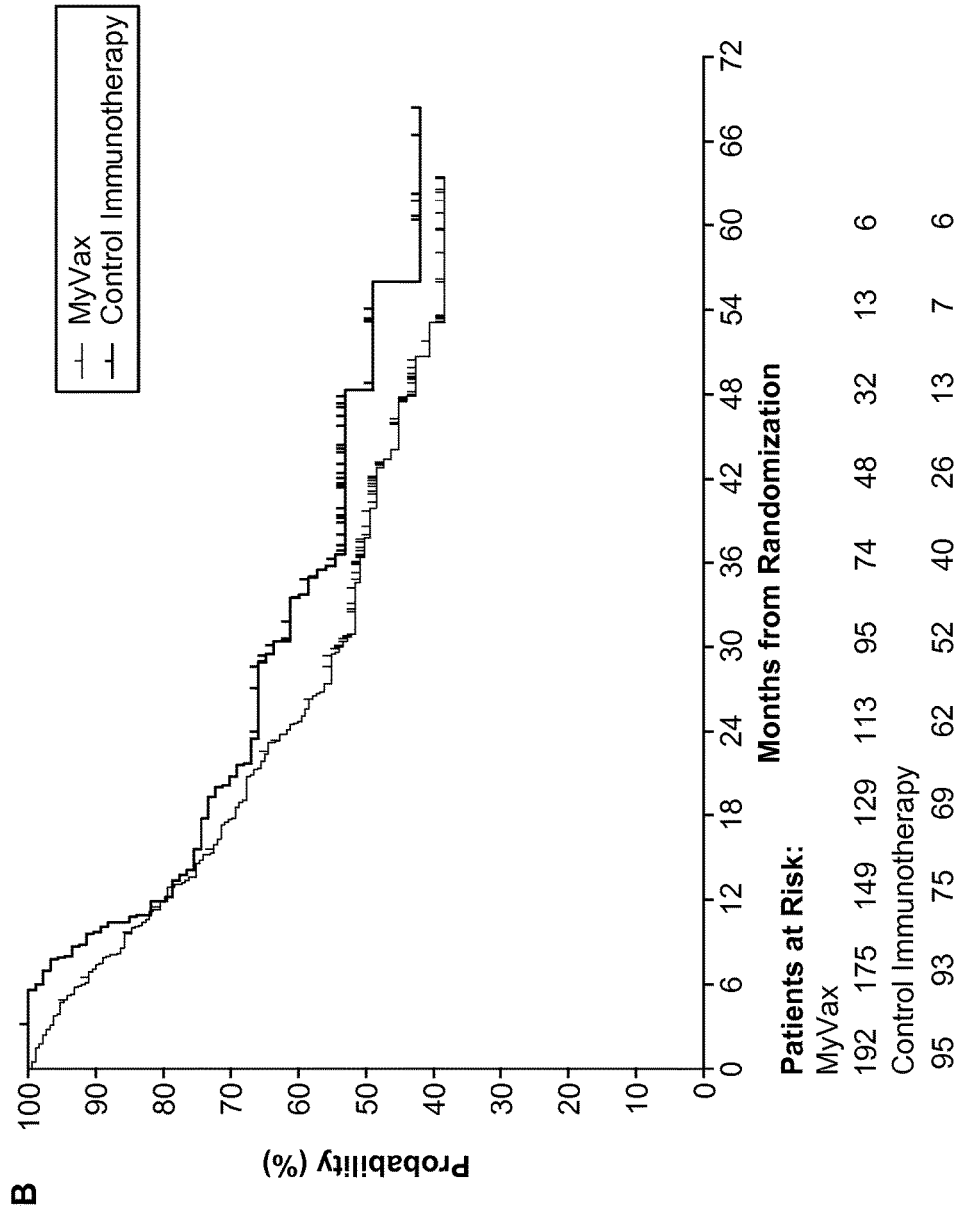
FIG. 2 (Cont. 1)

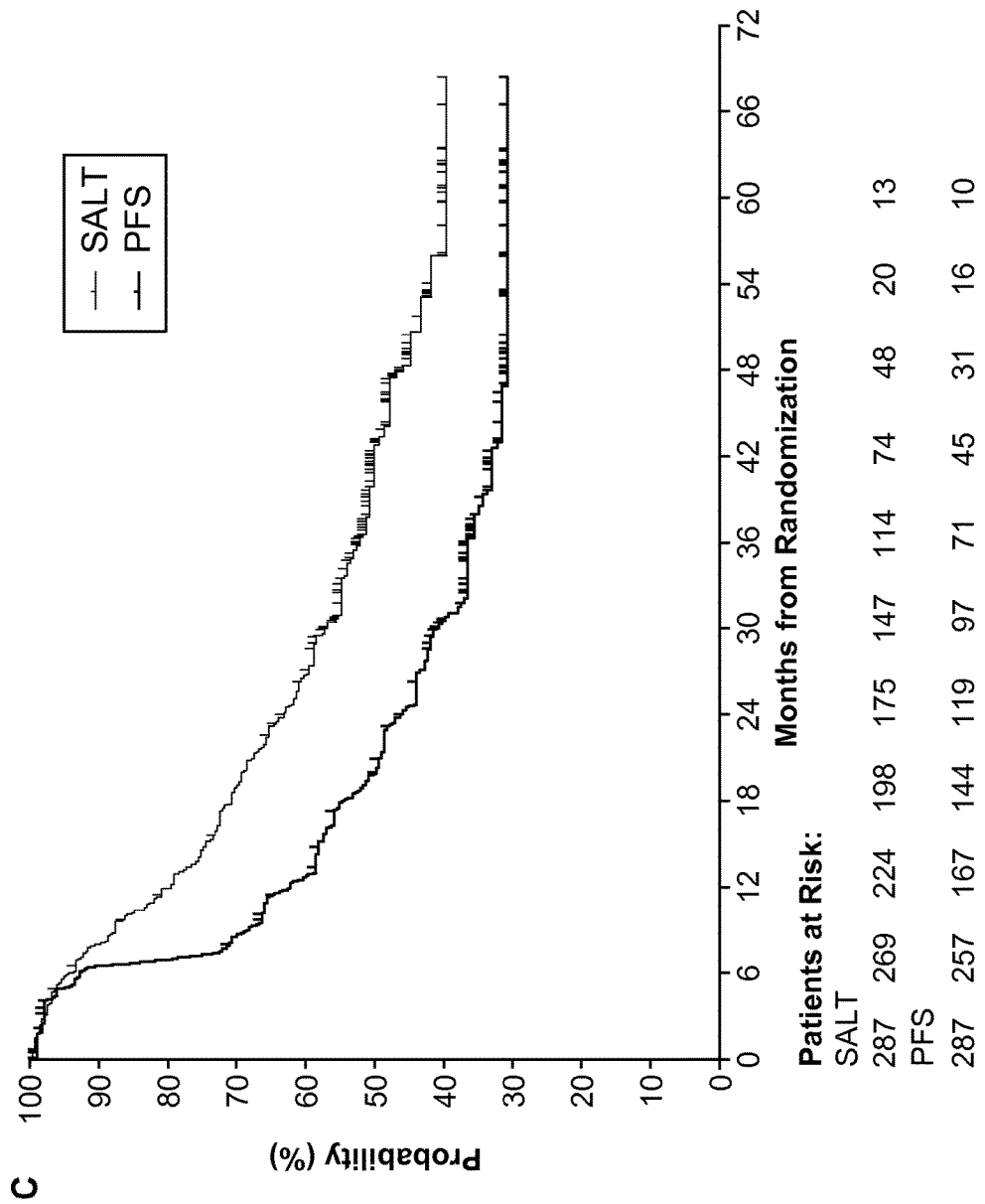
FIG. 2 (Cont. 2)

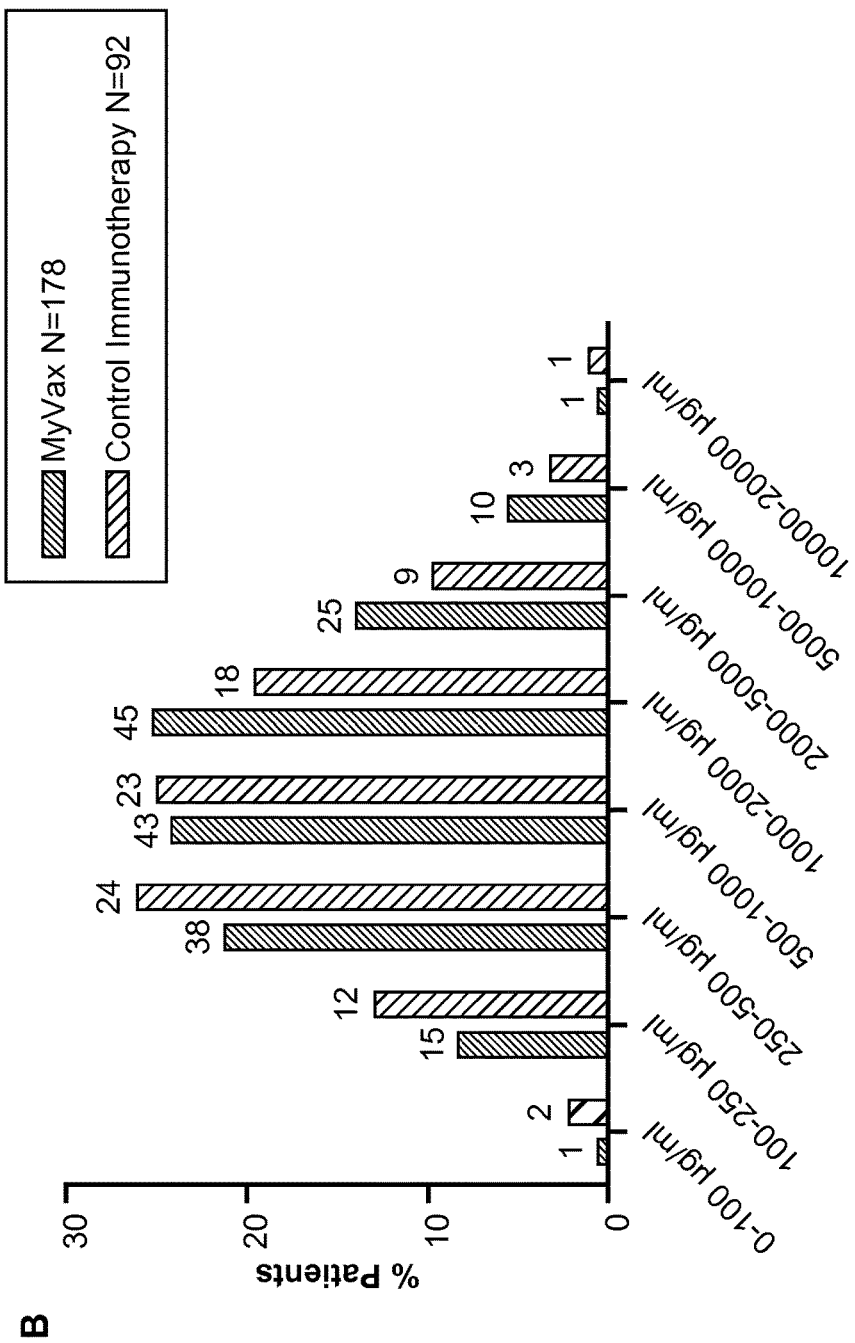
FIG. 4 (Cont. 1)

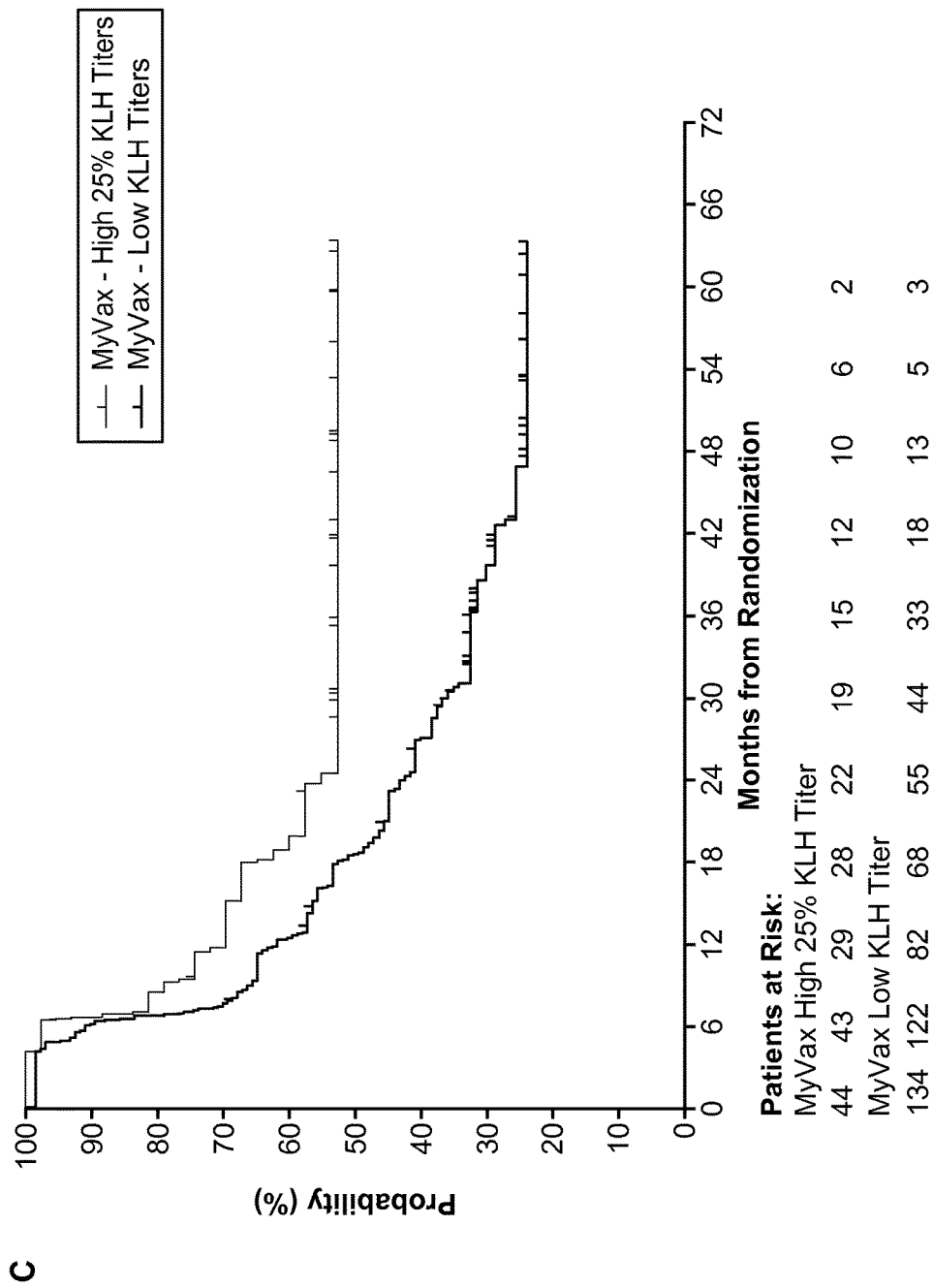
FIG. 4 (Cont. 2)

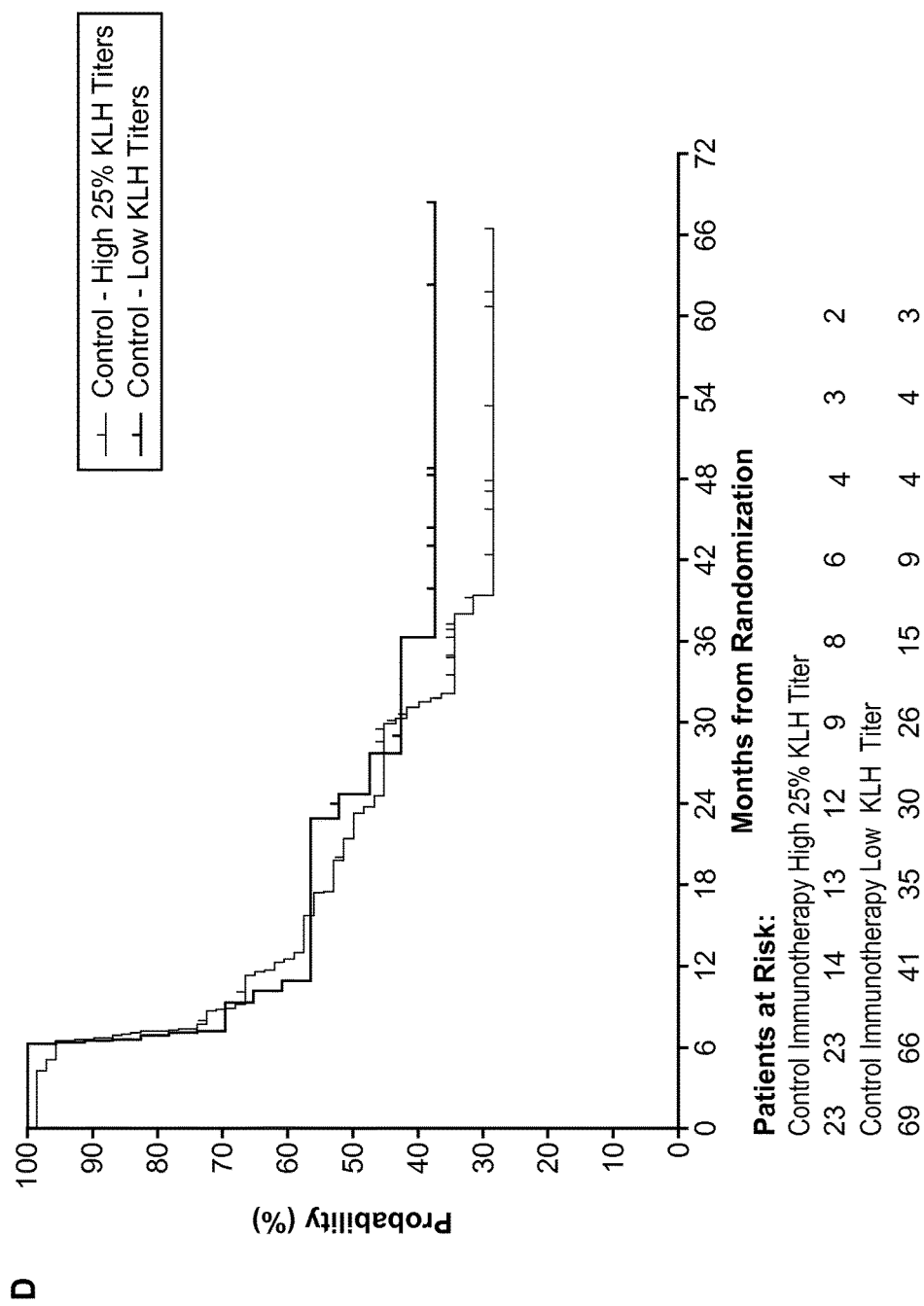
FIG. 4 (Cont. 3)

METHOD OF PREDICTING RESPONSIVENESS OF B CELL LINEAGE MALIGNANCIES TO ACTIVE IMMUNOTHERAPY

FEDERALLY SPONSORED RESEARCH AND DEVELOPMENT

This invention was made with Government support under contract CA034233 awarded by the National Institutes of Health. The Government has certain rights in this invention.

BACKGROUND OF THE INVENTION

Lymphomas represent about 4% of the new cases of cancer diagnosed in the United States each year, making them the fifth most common cancer diagnosis and a leading cause of cancer death. About 60,000 individuals are diagnosed with lymphoma every year, of which about 90% are Non-Hodgkin Lymphomas (NHLs), with the remainder being Hodgkin Lymphoma (HL). In fact, while the incidence of most cancers is decreasing, lymphoma is one of only two tumors increasing in frequency, although the cause for this increase is unknown.

Non-Hodgkin lymphomas are a heterogeneous group of disorders involving malignant monoclonal proliferation of lymphoid cells in lymphoreticular sites, including lymph nodes, bone marrow, the spleen, the liver, and the gastrointestinal tract. Presenting symptoms usually include peripheral lymphadenopathy. Compared with Hodgkin lymphoma, there is a greater likelihood of disseminated disease at the time of diagnosis. However, NHL is not one disease but rather a category of lymphocyte malignancies. These types can be divided into aggressive (fast-growing) and indolent (slow-growing) types, and they can be formed from either B-cells or T-cells. B-cell non-Hodgkin lymphomas include Burkitt lymphoma, chronic lymphocytic leukemia/small lymphocytic lymphoma (CLL/SLL), diffuse large B-cell lymphoma, follicular lymphoma, precursor B-lymphoblastic lymphoma, and mantle cell lymphoma, among others. T-cell non-Hodgkin lymphomas include mycosis fungoides, anaplastic large cell lymphoma, and precursor T-lymphoblastic lymphoma. Lymphomas that occur after bone marrow or stem cell transplantation are usually B-cell non-Hodgkin lymphomas. Prognosis and treatment depend on the stage and type of disease.

Although NHL usually respond initially to low dose chemotherapy and/or radiotherapy, relapses and treatment refraction occur after a period of months or years. Very high dose chemotherapy and/or radiotherapy with hematopoietic stem cell transplantation can induce longer remissions but unfortunately is substantially toxic, carries a high early mortality, and is not curative.

In B-cell lymphoma malignancies, a clonotypic surface immunoglobulin (Ig) expressed by malignant B-cells is known as an idiotype (Id) epitope. Id is a tumor-specific antigen and, therefore, provides a unique opportunity to target the tumor through a method of active immunotherapy, where the patient is vaccinated against the tumor-specific idiotype. Id proteins contain structures that can be recognized by antibodies and by CD4$^+$ and CD8$^+$ T cells and can be isolated from autologous tumor cells and formulated into a custom-made therapeutic tumor vaccine. A traditional approach for generating patient-specific Id vaccines involves fusion of individual patient's lymphoma cells with myeloma cells, yielding a 'rescue' hybridoma secreting large quantities of Id protein. The Id is then chemically conjugated to the highly immunogenic carrier protein keyhole limpet hemocyanin (KLH) rendering it more immunogenic. The resulting Id-KLH conjugate is then injected subcutaneously (s.c.) along with an immunologic adjuvant to evoke tumor-specific antibody and T cell responses.

Results from early clinical trials of Id immunization for follicular lymphoma using hybridoma-derived Id have included the induction of tumor-specific anti-Id immune responses that correlate with improved disease-free and overall survival, achievement of molecular complete remissions (bcl-2 negative PCR status) and favorable progression-free survival (PFS) using Id-KLH plus GM-CSF, and durable tumor regressions following immunization with Id protein-loaded autologous dendritic cells. However, limitations of the rescue hybridoma method include a production failure rate as high as 15%, the need for viable tumor cells for cell fusion, non-uniformity of the Id product (IgG, IgM or other isotype expressed by the tumor) and the instability of Id secretion by tumor hybridomas over time.

An alternative technique, 'molecular rescue', employs PCR amplification of the tumor-specific variable region Ig sequences from small numbers of tumor cells ($10^7$) for cloning into expression vectors carrying the desired immunoglobulin isotype backbone. This molecular approach obviates the need for surgical biopsy, as adequate material can be obtained by fine or core needle biopsy, bone marrow biopsy, involved peripheral blood or fluid collection aspiration. Phase I/II and III clinical trials have been performed with patient-specific therapeutic Id vaccines in patients with follicular NHL in first remission following chemotherapy.

However, significant variations in patient responsiveness have been found with anti-idiotype treatment, making it difficult to determine the optimal treatment for an individual. Although analysis of a pre-specified endpoint in the clinical trial data for personalized immunotherapy arm showed a highly statistically significant difference in the progression-free survival between patients who mounted a positive humoral immune response to the tumor-specific target and those who did not, there has not been a means of determining prior to therapy which patients will generate such serological responses. The present invention addresses the need for improved prognosis of patient responsiveness.

SUMMARY OF THE INVENTION

Predictive biomarkers are provided herein, which biomarkers identify those patients suffering from immunoglobulin positive (Ig$^+$) B lineage malignancies that will be responsive to active immunotherapy, where the active immunotherapy comprises vaccination with a tumor-specific idiotype-immunogen. It is shown herein that patient responsiveness to the idiotype-immunogen is dependent upon the sequence of the immunogen, where an immunogen having a low number of tyrosine residues in the CDR1 (herein termed CDR1-Y$^{lo}$) regions of one or both of the immunogen heavy and light chains is predictive of a positive anti-tumor clinical response, while a high number of CDR1 tyrosine residues (herein termed CDR1-Y$^{hi}$) is predictive of a low anti-tumor clinical response. A positive anti-tumor clinical response is generally considered to be a progression-free survival time greater than that of a control, e.g. a placebo treated individual. A positive anti-tumor clinical response is often, but not entirely, correlated with a high-titer host humoral immune response to immunization with an idiotype-immunogen. The classification of a patient by the methods of the invention may be used to select a suitable therapy for the patient.

In certain embodiments, the method of the invention comprises obtaining a biological sample from a patient suspected of having an Ig+ B lineage malignancy, which biological sample comprises tumor cells; enumerating the number of tyrosine residues in one or both of the Ig heavy and Ig light chain CDR1 regions; comparing the number of tyrosine residues to a reference number; and predicting the responsiveness of the patient to active immunotherapy based on the number of CDR1 (H+L) tyrosine residues, where a patient with greater than 3 CDR1 (H+L) tyrosine residues is predicted to be non-responsive. Specifically, a patient with 3 or more CDR1 (H+L) tyrosine residues is predicted to usually not generate humoral responses to the immunogen, and independently of whether mounting such humoral responses, to have a tendency for adverse outcomes. Based on such a prediction a suitable treatment is selected for a patient, where generally patients predicted to be responsive to active immunotherapy may be provided with such active immunotherapy, and patients predicted to be non-responsive will be provided with other methods of treatment, e.g. chemotherapy, radiation therapy, passive immunotherapy, and the like.

In some embodiments of the invention, nucleic acids, e.g. DNA, mRNA, particularly mRNA encoding a tumor-specific idiotype, is obtained from the tumor cells in the patient biological sample, and prepared in a method suitable for sequence determination. The genetic sequence encoding the tumor-specific idiotype is analyzed for the presence of tyrosine residues in the CDR1 region. In some embodiments the analysis includes sequencing the coding sequence across the CDR1 region of the heavy chain, the light chain, or preferably both. In other embodiments, tyrosine enumeration may be performed by hybridization to specific primers, and the like, as known in the art. In other embodiments, the enumeration of tyrosine residues comprises analysis of the encoded polypeptide, e.g. by mass spectrometry, western blot analysis, and the like.

In some embodiments of the invention, the B lineage malignancy is a non-Hodgkin's lymphoma (NHL). In certain embodiments the NHL is a follicular lymphoma.

DEFINITIONS

Figure 1:
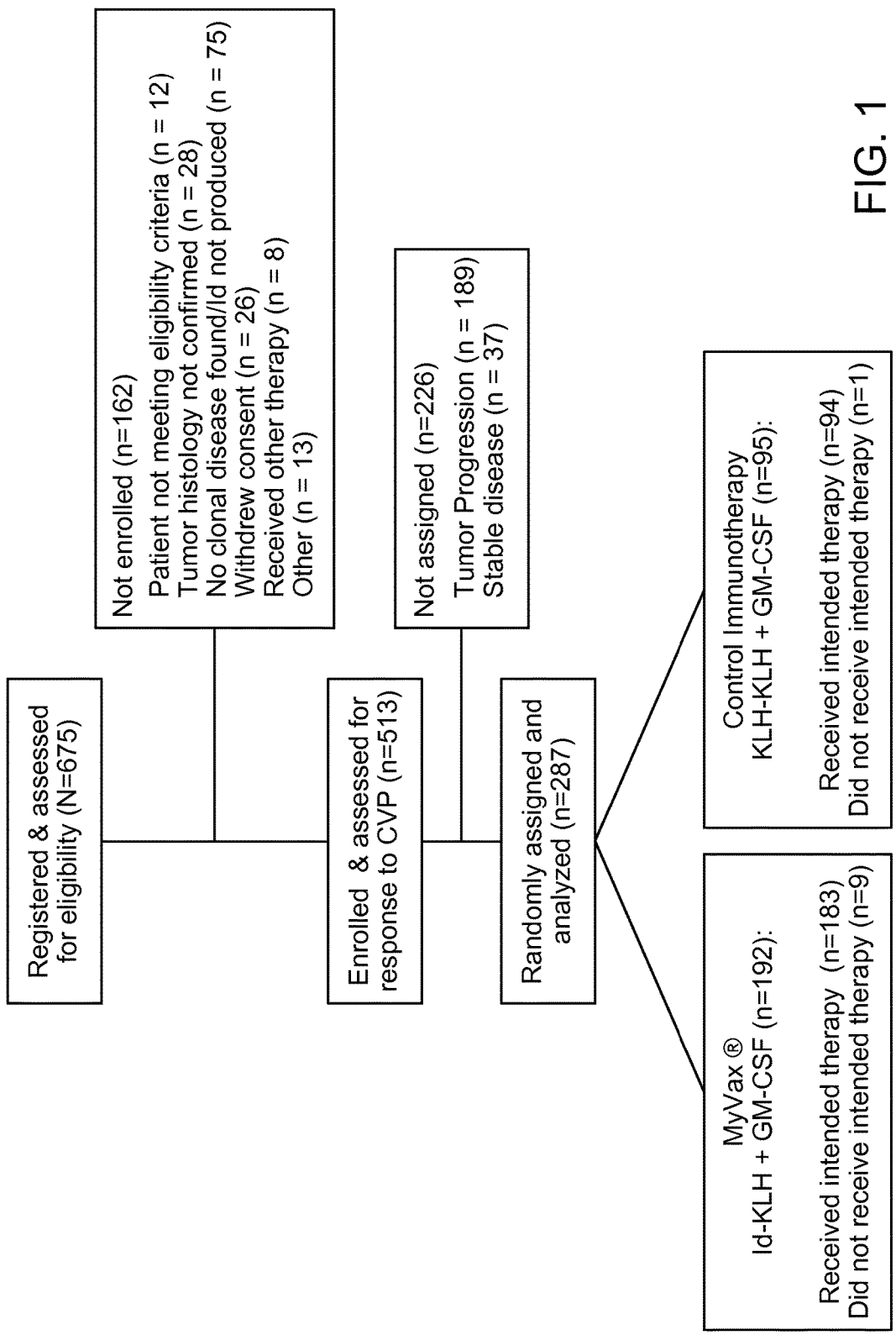
FIG. 1: Distribution of patient disposition per conventions of Consolidated Standards of Reporting Trials (CONSORT). Among patients with tumor progression prior to randomization (n=189), 52 patients received <8 cycles of chemotherapy, 20 patients had progressive disease (PD) immediately after chemotherapy, 117 patients achieved a response but had PD between the post-chemotherapy assessment and randomization. Among those randomized, 9 in the MyVax arm were no immunized due to PD prior to planned 1st immunization; 1 patient in the Control Immunotherapy erroneously received a single injection of MyVax, but was nonetheless considered among those in the Control Immunotherapy arm in the intention to treat analyses. Id-KLH, idiotype conjugated to keyhole limpet hemocyanin; GM-CSF, granulocyte-macrophage colony-stimulating factor.

To facilitate an understanding of the invention, a number of terms are defined below.

As used herein "idiotype" refers to an epitope in the hypervariable region of an immunoglobulin chain, including but not limited to an epitope formed by contributions from both the light chain and heavy chain CDRs. A "non-idiotypic portion" refers to an epitope located outside the hypervariable regions, such as the framework regions.

As used herein "immunoglobulin" refers to any of a group of large glycoproteins that are secreted by plasma cells and that function as antibodies in the immune response by binding with specific antigens. The specific antigen bound by an immunoglobulin may or may not be known. There are five classes of immunoglobulins: IgA, IgD, IgE, IgG, and IgM.

The term "antibody," as used herein, is intended to refer to immunoglobulin molecules comprised of four polypeptide chains, two heavy (H) chains and two light (L) chains (lambda or kappa) inter-connected by disulfide bonds. An antibody has a known specific antigen with which it binds. Each heavy chain of an antibody is comprised of a heavy chain variable region (abbreviated herein as HCVR, HV or VH) and a heavy chain constant region. The heavy chain constant region is comprised of three domains, CH1, CH2 and CH3. Each light chain is comprised of a light chain variable region (abbreviated herein as LCVR or VL or KV or LV to designate kappa or lambda light chains) and a light chain constant region. The light chain constant region is comprised of one domain, CL. The VH and VL regions can be further subdivided into regions of hypervariability, termed complementarity determining regions (CDRs), interspersed with regions that are more conserved, termed framework regions (FR). Each variable region (VH or VL) contains 3 CDRs, designated CDR1, CDR2 and CDR3. Each variable region also contains 4 framework sub-regions, designated FRl, FR2, FR3 and FR4.

As used herein, the term "antibody fragments" refers to a portion of an intact antibody. Examples of antibody fragments include, but are not limited to, linear antibodies, single-chain antibody molecules, Fv, Fab and F(ab').sub.2 fragments, and multispecific antibodies formed from antibody fragments. The antibody fragments preferably retain at least part of the heavy and/or light chain variable region.

As used herein, the terms "complementarity determining region" and "CDR" refer to the regions that are primarily responsible for antigen-binding. There are three CDRs in a light chain variable region (CDRL1, CDRL2, and CDRL3), and three CDRs in a heavy chain variable region (CDRH1, CDRH2, and CDRH3). The particular designation in the art for the exact location of the CDRs varies depending on what definition is employed. Preferably, the IMGT designations are used (see Brochet et al. (2008) Nucleic Acids Res. 36:W503-8, herein specifically incorporated by reference), which uses the following designations for both light and heavy chains: residues 27-38 (CDR1), residues 56-65 (CDR2), and residues 105-116 (CDR3); see also Lefranc, M P, The Immunologist, 7:132-136, 1999, herein incorporated by reference.

The residues that make up the six CDRs have also been characterized by Kabat and Chothia as follows: residues 24-34 (CDRL1), 50-56 (CDRL2) and 89-97 (CDRL3) in the light chain variable region and 31-35 (CDRH1), 50-65 (CDRH2) and 95-102 (CDRH3) in the heavy chain variable region; Kabat et al., (1991) Sequences of Proteins of Immunological Interest, 5th Ed. Public Health Service, National Institutes of Health, Bethesda, Md., herein incorporated by reference; and residues 26-32 (CDRL1), 50-52 (CDRL2) and 91-96 (CDRL3) in the light chain variable region and 26-32 (CDRH1), 53-55 (CDRH2) and 96-101 (CDRH3) in the heavy chain variable region; Chothia and Lesk (1987) J. Mol. Biol. 196: 901-917, herein incorporated by reference. Unless otherwise specified, the terms "complementarity determining region" and "CDR" as used herein, include the residues that encompass IMGT, Kabat and Chothia definitions. Also, unless specified, as used herein, the numbering of CDR residues is according to IMGT.

As used herein, the term "framework" refers to the residues of the variable region other than the CDR residues as defined herein. There are four separate framework sub-regions that make up the framework: FR1, FR2, FR3, and FR4 (See non-underlined regions in FIGS. 6-11). In order to indicate if the framework sub-region is in the light or heavy chain variable region, an "L" or "H" may be added to the sub-region abbreviation (e.g., "FRL1" indicates framework sub-region 1 of the light chain variable region). Unless specified, the numbering of framework residues is according to IMGT.

As used herein, "antigen" refers to any substance that, when introduced into a body, e.g., of a patient or subject, stimulates an immune response such as the production of an antibody that recognizes the antigen.

As used herein, the term "immunogenic composition" refers to a composition comprising an antigen.

As used herein, the term "vaccine" refers to a composition comprising an antigen for use as a therapy or treatment to induce an immune response. Vaccines may be used both prophylactically (for prevention of disease) and therapeutically (for the treatment of existing disease). For example, with respect to cancer therapies, a therapeutic vaccine would generally be given to a cancer patient to induce an immune response to fight the cancer, e.g., by attacking the patient's malignant cells, while a prophylactic vaccine would generally be given to an individual who does not have a particular type of cancer to induce an immune response to prevent that type of cancer, e.g., by attacking viruses known to cause that type of cancer.

The term "passive immunotherapy" as used herein refers to therapeutic treatment of a subject or patient using immunological agents such as antibodies (e.g., monoclonal antibodies) produced outside a subject or patient, without the purpose of inducing the subject or patient's immune system to produce a specific immune response to the therapeutic agent.

The term "active immunotherapy" as used herein refers to therapeutic treatment of a subject or patient to induce the subject or patient's immune system to produce a specific immune response, e.g., to a protein derived from a malignant cell. In preferred embodiments, the immunogenic composition used in active immunotherapy comprises one or more antigens derived from a subject's malignant cells. In some particularly preferred embodiments, the immunogenic agent comprises at least a portion of an immunoglobulin derived from a subject's malignant cell. It is understood by those of skill in the art that, as used in active immunotherapy, an immunoglobulin derived from a patient or subject's malignant cell is generally used as an antigen, not as an antibody intended to act as a therapeutic agent in passive immunotherapy.

As used herein, the terms "subject" and "patient" refer to any animal, such as a mammal like a dog, cat, bird, livestock, and preferably a human.

As used herein, the terms "an oligonucleotide having a nucleotide sequence encoding a polypeptide," "polynucleotide having a nucleotide sequence encoding a polypeptide," and "nucleic acid sequence encoding a peptide" means a nucleic acid sequence comprising the coding region of a particular polypeptide. The coding region may be present in a cDNA, genomic DNA, or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc., or a combination of both endogenous and exogenous control elements.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated (e.g. host cell proteins).

As used herein, the terms "portion" when used in reference to a nucleotide sequence (as in "a portion of a given nucleotide sequence") refers to fragments of that sequence. The fragments may range in size from ten nucleotides to the entire nucleotide sequence minus one nucleotide (e.g., 10 nucleotides, 20, 30, 40, 50, 100, 200, etc.).

As used herein, the term "portion" when in reference to an amino acid sequence (as in "a portion of a given amino acid sequence") refers to fragments of that sequence. The fragments may range in size from six amino acids to the entire amino acid sequence minus one amino acid (e.g., 6 amino acids, 10, 20, 30, 40, 75, 200, etc.)

As used herein, the term "purified" or "to purify" refers to the removal of contaminants from a sample. For example, monoclonal antibodies reactive with a framework epitope of an immunoglobulin may be purified by removal of contaminating non-immunoglobulin proteins; they are also purified by the removal of immunoglobulins that do not bind to the same antigen. The removal of non-immunoglobulin proteins and/or the removal of immunoglobulins that do not bind the particular antigen results in an increase in the percentage of antigen specific immunoglobulins in the sample. In another example, recombinant antigen-specific polypeptides are expressed in bacterial host cells and the polypeptides are purified by the removal of host cell proteins; the percentage of recombinant antigen-specific polypeptides is thereby increased in the sample.

As used herein, the terms "treat," "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, e.g., causing regression of the disease, e.g., to completely or partially remove symptoms of the disease.

Cancer is "inhibited" if at least one symptom of the cancer is alleviated, terminated, slowed, or prevented. As used herein, cancer is also "inhibited" if recurrence or metastasis of the cancer is reduced, slowed, delayed, or prevented. Similarly, a person with cancer is "responsive" to a treatment if at least one symptom of the cancer is alleviated, terminated, slowed, or prevented. As used herein, a person with cancer is also "responsive" to a treatment if recurrence or metastasis of the cancer is reduced, slowed, delayed or prevented.

A biopsy sample suitable for use in the methods described herein is one that is collected from a tumor from a person with B-lineage malignancy, which may be a lymphoma, leukemia, or plasmacytoma. A lymphoma is a solid neoplasm of lymphocyte origin, and is most often found in the lymphoid tissue. Thus, for example, a biopsy from a lymph node, e.g. a tonsil, containing such a lymphoma would constitute a suitable biopsy. In one embodiment, the B cell lymphoma is a follicular lymphoma. Other B cell malignancies include multiple myeloma, diffuse large B cell lymphoma; mucosa-Associated lymphatic tissue lymphoma (MALT); small cell lymphocytic lymphoma; mantle cell lymphoma (MCL); Burkitt lymphoma; mediastinal large B cell lymphoma; waldenstrom macroglobulinemia; nodal marginal zone B cell lymphoma (NMZL); pplenic marginal zone lymphoma (SMZL); intravascular large B-cell lymphoma; primary effusion lymphoma; lymphomatoid granulomatosis, etc.

"Immunohistochemistry" as used herein refers to the technique of visualizing the presence of a polypeptide in a cell in a tissue with an antibody that is specific for the polypeptide. Generally, the tissue is fixed, thinly sliced, and incubated with the antibody, during which time the antibody will hybridize to the target polypeptide. Unbound antibody is washed away and the bound antibody is visualized, either directly or indirectly, by microscopy.

Before the present active agents and methods are described, it is to be understood that this invention is not limited to the particular methodology, products, apparatus and factors described, as such methods, apparatus and formulations may, of course, vary. It is also to be understood that the terminology used herein is for the purpose of describing particular embodiments only, and is not intended to limit the scope of the present invention which will be limited only by appended claims.

It must be noted that as used herein and in the appended claims, the singular forms "a," "and," and "the" include plural referents unless the context clearly dictates otherwise. Thus, for example, reference to "a drug candidate" refers to one or mixtures of such candidates, and reference to "the method" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, formulations and methodologies which are described in the publication and which might be used in connection with the presently described invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

Generally, conventional methods of protein synthesis, recombinant cell culture and protein isolation, and recombinant DNA techniques within the skill of the art are employed in the present invention. Such techniques are explained fully in the literature, see, e.g., Maniatis, Fritsch & Sambrook, Molecular Cloning: A Laboratory Manual (1982); Sambrook, Russell and Sambrook, Molecular Cloning: A Laboratory Manual (2001); Harlow, Lane and Harlow, Using Antibodies: A Laboratory Manual: Portable Protocol NO. I, Cold Spring Harbor Laboratory (1998); and Harlow and Lane, Antibodies: A Laboratory Manual, Cold Spring Harbor Laboratory; (1988).

DETAILED DESCRIPTION OF THE EMBODIMENTS

The present invention provides predictive biomarkers that identify those patients suffering from immunoglobulin positive ($Ig^+$) B lineage malignancies that will be responsive to active immunotherapy, where the active immunotherapy comprises vaccination with a tumor-specific idiotype-immunogen. An immunogen having a low number of tyrosine residues in the CDR1 (herein termed CDR1-$Y^{lo}$) regions of one or both of the immunogen heavy and light chains is predictive of a positive anti-tumor response, while a high number of CDR1 tyrosine residues (herein termed CDR1-$Y^{hi}$) is predictive of a low anti-tumor response.

The present invention demonstrates the enumeration of amino acids across the seven topographically constrained regions in each patient's idiotypic sequence; considering the tumor's unique immunoglobulin heavy and light chain genes. These regions are termed Framework regions 1 through 4 [FR1/2/3/4], and Complementarity Determining Regions 1 through 3 [CDR1/2/3]. It was determined whether any sequence features were differentially distributed among patients mounting immune responses (Id-R) or failing to mount them (Id-NR). The tyrosine frequency emerged as a dominant finding, and it was found that the frequency of tyrosines in CDR1 of both heavy and light chains is highly significantly associated with immune response. There is a significant co-dominant effect between the heavy and light chains such that an excess within either heavy or light chain contributes to poor immune responses.

The number of tyrosines within CDR1 of heavy and light chains is continuously associated with probability of mounting a significant humoral immune response using pre-specified criteria, with the magnitude of this immune response, as well as with Progression Free Survival (PFS) in a univariate Cox regression.

While the continuous relationships between the tyrosine count of CDR1 in heavy and light chains are biologically compelling, a clinical decision tool beneficially provides a discrete threshold. Therefore, for each patient, a threshold of 3 or more tyrosines in aggregate (when considering CDR1 of their Heavy and Light chains) was determined to predict lack of a humoral immune response. This threshold is selected relative to the median number of tyrosines observed in the CDR1 regions of the paired heavy and light chain idiotypes across a large cohort of patients with lymphoma. Consistent with these thresholds, when combining the heavy and light chain CDR1 Y count and applying Receiver Operator Curve analyses, more than 2 tyrosines in CDR1 (for discriminating CDR1-$Y^{hi}$ from CDR1-$Y^{lo}$) had the best performance in predicting immune response.

The CDR H1+L Y-count has ability not only to predict immune response, but also to independently predict progression free survival (PFS). Even among the Id-R and Id-NR subgroups, the number of tyrosines in CDR H1/L1 predicts PFS. These observations hold exclusively in the vaccinated patients and not the placebo control arm.

The tyrosine-count is thus predictive of clinical benefit conferred by the active immunization, and not simply a prognostic biomarker serving as a proxy for underlying heterogeneity among tumors, supported by a lack of association between this tyrosine frequency and known factors influencing outcomes of patients with follicular lymphoma, including histological grade, and the Follicular Lymphoma International Prognostic Index [FLIPI].

Conditions of Interest for Prognosis

The invention provides methods of prognosis to determine whether a patient will have an effective anti-tumor response to active immunotherapy, where the active immunotherapy comprises vaccination with a tumor-specific idiotype-immunogen. Conditions for which the methods of the invention find use are those leukemias, lymphomas and plasmacytomas that express an immunoglobulin, e.g. comprising a tumor-specific idiotype. In some embodiments the tumor-specific idiotype is displayed on the cell surface of the tumor cell.

B cell lymphomas are a heterogeneous group of disorders involving malignant monoclonal proliferation of lymphoid cells in lymphoreticular sites, including lymph nodes, bone marrow, the spleen, the liver, and the GI tract. Presenting symptoms usually include peripheral lymphadenopathy. There is a likelihood of disseminated disease at the time of diagnosis. Diagnosis is usually based on lymph node or bone marrow biopsy or both. Conventional treatment involves radiation therapy, chemotherapy, or both.

Specific B cell lymphomas of interest include, without limitation, multiple myeloma, diffuse large B cell lymphoma; follicular lymphoma; mucosa-Associated lymphatic tissue lymphoma (MALT); small cell lymphocytic lymphoma; mantle cell lymphoma (MCL); Burkitt lymphoma; mediastinal large B cell lymphoma; waldenstrom macroglobulinemia; nodal marginal zone B cell lymphoma (NMZL); pplenic marginal zone lymphoma (SMZL); intravascular large B-cell lymphoma; primary effusion lymphoma; lymphomatoid granulomatosis, etc.

The CDR1 tyrosine enumeration may be generated from a biological sample using any convenient protocol, for example as described below. In the methods of the invention, the CDR1 region in a tumor-specific idiotype is delineated on the immunoglobulin protein itself, or on a coding sequence generated from tumor cell mRNA, cDNA, chromosomal DNA, etc., usually cDNA obtained from reverse transcription of tumor cell mRNA. Methods of delineating the CDR1 region are described above, and are known in the art. As is conventional in the art, an in-frame TAT or TAC codon provides for a tyrosine residue.

Samples can be obtained from the tissues or fluids of an individual. For example, samples can be obtained from whole blood, lymph or bone marrow biopsy, etc. Prognostic samples are collected any time after an individual is suspected to have an autoimmune disease or has exhibited symptoms that predict such a disease. For example, for a B-cell lymphoma patient, suitable tumor samples may be obtained, e.g., by surgical biopsy of an enlarged lymph node (LN) or other extranodal tissue involved by lymphoma, by fine needle aspiration (FNA) of an enlarged LN, by phlebotomy or aspirate of a patient whose blood or other fluids contains greater than about $5 \times 10^6$ lymphoma cells/mL (quantified by manual differential); or 4) bone marrow (BM) aspiration when the patient's BM contains greater than about 30% involvement (percentage of total inter-trabecular space).

In particular embodiments, the present invention provides methods for prognosis comprising: obtaining a polynucleotide sequence of the variable region of the immunologic receptor from a sample comprising the malignant cells; comparing the polynucleotide sequence to reference sequences of the immunologic antigen receptor to delineate the CDR1 region; enumerating the CDR1 tyrosine residues; wherein the patient is prognosed as responsive to active immunotherapy if the total number of heavy and light chain CDR1 Y residues is 3 or less, usually less than 3. Alternatively a patient is prognosed as responsive if the number of heavy chain CDR1 Y is less than 2; and/or if the light chain CDR1 Y is less than one. Any suitable method used in the art may be utilized for sequence determination. Such methods may include reverse transcription and amplification of tumor cell mRNA, followed by sequence determination, including sequencing by hybridization. The sequence thus obtained is aligned for delineation of the CDR1 region, and the open reading frame analyzed for the presence of tyrosine codons. In certain embodiments, the sample is a biopsy sample. In additional embodiments, the sample comprises less than about 50% malignant cells. In further embodiments, the sample comprises less than about 10% malignant cells.

Where the immunoglobulin protein itself is analyzed, a biochemical method may be applied to separate the CDR1 from the rest of the sequence, following by western blotting or mass spectroscopy to enumerate the tyrosines. Alternatively a specific modification to the tyrosines within CDR1 (eg, sulfonation, nitrosylation, phosphorylation, glycosylation) may be detected with a monoclonal antibody, or manifested as a spectral shift on MALDI or SELDI TOF.

The detection reagents can be provided as part of a kit. Thus, the invention further provides kits for tyrosine enumeration in a biological sample. Procedures using these kits can be performed by clinical laboratories, experimental laboratories, medical practitioners, or private individuals. The kits of the invention may comprise amplification and/or sequencing primers, and/or hybridization primers. The kit may optionally provide additional components that are useful in the procedure, including, but not limited to, buffers, developing reagents, labels, reacting surfaces, means for detection, control samples, standards, instructions, and interpretive information.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, hard-drive, network data storage, etc., on which the information has been recorded. Yet another means that may be present is a website address which may be used via the internet to access the information at a removed site. Any convenient means may be present in the kits.

Therapy

The present invention provides for the selection of therapeutic treatments for patients suffering from Ig$^+$ B lineage malignancies, where a patient is first analyzed by the methods of the invention to determine responsiveness to active immunotherapy. Patients have a positive prognosis for active immunotherapy may be treated by the administration of an immunogenic composition comprising at least a portion of the same lymphoma cell surface immunoglobulin.

In certain embodiments, a patient is treated with immunogenic compositions to induce the patient's immune system to produce a specific immune response to a malignancy. In some preferred embodiments, the immunogenic composition used in active immunotherapy comprises one or more antigens derived from a patient malignant cells. In some particularly preferred embodiments, the immunogenic composition comprises at least an idiotypic portion of an immunoglobulin derived from a subject's own malignant cell(s). For example, B-cell lymphoma cells have on their surface particular immunoglobulins. These immunoglobulins, particularly the idiotypic portions ("idiotypic proteins") can be used as antigens in immunogenic compositions to produce patient-specific idiotypic vaccines. In certain embodiments, the idiotypic proteins are produced recombinantly. In some embodiments, particular individual recombinant idiotypic proteins are selected for use, while in other embodiments, multiple, tumor-specific idiotypic proteins are used in a multivalent composition (see, e.g., U.S. Pat. No. 5,972,334 to Denney, issued Oct. 25, 1999, incorporated by reference herein in its entirety). In certain embodiments, the idiotypic protein is a recombinant idiotype (Id) immunoglobulin (Ig) derived from a patient's B-cell lymphoma, for example an IgG with either a kappa (κ) or a lambda (λ) light chain, obtained from each patient. In preferred embodiments, the immunogenic composition comprises the same heavy and light chain V region sequences expressed by the patient's tumor.

In certain embodiments, the idiotypic protein is conjugated to a carrier, e.g., a protein using techniques which are well-known in the art. Materials that are commonly chemically coupled to the antigens e.g., to enhance antigenicity, include keyhole limpet hemocyanin (KLH), thyroglobulin (THY), bovine serum albumin (BSA), ovalbumin (OVA), tetanus toxoid (TT), diphtheria toxoid, and tuberculin purified protein derivative. In preferred embodiments, KLH manufactured under cGMP conditions is obtained from biosyn Arzneimittel GmbH and used for the preparation of Id-KLH conjugates.

In some embodiments, a cytokine is linked to the idiotypic protein. In certain embodiment, the immunogenic composition produced comprises a fusion protein comprising the idiotypic protein and a cytokine such as GM-CSF, IL-2 or IL-4 (see, e.g., PCT International Application PCT/US93/09895, Publication No. WO 94/08601 and Tao and Levy (1993) Nature 362:755 and Chen et al. (1994) J. Immunol. 153:4775; all of which are herein incorporated by reference). Generally in such fusion proteins, sequences encoding the desired cytokine are added to the 3' end of sequences encoding the idiotypic protein.

In some embodiments, the antibodies are conjugated to various radiolabels for both diagnostic and therapeutic purposes. Radiolabels allow "imaging" of tumors and other tissue, as well helping to direct radiation treatment to tumors. Exemplary radiolabels include, but are not limited to, $^{131}$I, $^{125}$I, $^{123}$I, $^{99}$Tc, $^{67}$Ga, $^{111}$In, $^{188}$Re, $^{186}$Re, and preferably, $^{90}$Y.

In certain embodiments, the subject has measurable tumor burden prior to treatment and exhibits at least a 25% reduction in tumor burden after treatment (e.g. at least 25%, 30%, 40% or between 25-40%). In other embodiments, the subject has a measurable tumor burden prior to treatment and exhibits at least a 50% reduction in tumor burden after treatment (e.g. at least 50%, 60%, 70%, 80%, or 90%). In some embodiments, the treatment results in less than 25% depletion of normal B cells in the subject (e.g., less than 25%, less than 20%, less than 15%, less than 10% or less than 5%). In particular embodiments, the treatment results in less than 15% depletion of normal B cells in the subject.

In certain embodiments, the disease treated is Non-Hodgkin's lymphoma (NHL). In other embodiments, the disease treated includes any immunoglobulin expressing B cell malignancy. In some embodiments, the disease is selected from relapsed Hodgkin's disease, resistant Hodgkin's disease high grade, low grade and intermediate grade Non-Hodgkin's lymphomas (NHLs), B cell chronic lymphocytic leukemia (B-CLL), lymphoplasmacytoid lymphoma (LPL), mantle cell lymphoma (MCL), follicular lymphoma (FL), diffuse large cell lymphoma (DLCL), Burkitt lymphoma (BL), AIDS-related lymphomas, monocytic B cell lymphoma, angioimmunoblastic lymphoadenopathy, small lymphocytic; follicular, diffuse large cell; diffuse small cleaved cell; large cell immunoblastic lymphoblastoma; small, non-cleaved; Burkitt and non-Burkitt; follicular, predominantly large cell; follicular, predominantly small cleaved cell; follicular, mixed small cleaved and large cell lymphomas, and systemic lupus erythematosus (SLE). In particular embodiments, the disease treated is Waldenstrom's Macroglobulinemia (WM) or Chronic Lymphocytic Leukemia (CLL).

Active immunotherapy may be administered a part of a chemotherapeutic program (e.g. CHOP), whether before or after. The active immunotherapy may also be administered before, after or with cytokines, G-CSF, or IL-2 (See, U.S. Pat. No. 6,455,043, herein incorporated by reference).

The antibodies and antibody fragments of the present invention may be administered by any suitable means, including parenteral, non-parenteral, subcutaneous, topical, intraperitoneal, intrapulmonary, intranasal, and intralesional administration (e.g., for local immunosuppressive treatment). Parenteral infusions include, but are not limited to, intramuscular, intravenous, intra-arterial, intraperitoneal, or subcutaneous administration. In addition, antibodies are suitably administered by pulse infusion, particularly with declining doses. Preferably, the dosing is given by injections, most preferably intravenous or subcutaneous injections, depending in part on whether the administration is brief or chronic.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is advantageous to formulate parenteral compositions in dosage unit form for ease of administration and uniformity of dosage. The dosages of the antibodies of the present invention are generally dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of an antibody or antibody fragment is 0.1-20 mg/kg, more preferably 1-10 mg/kg. In some embodiments, the dosage is from 50-600 mg/m$^2$ (e.g. 375 mg/m$^2$). It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the present invention.

The dosage administered will, of course, vary depending upon known factors such as the pharmacodynamic characteristics of the particular agent, its mode and route of administration, the age, health, and weight of the recipient, the nature and extent of symptoms, the kind of concurrent treatment, the frequency of treatment, and the effect desired. For example, a daily dosage of active ingredient can be about 0.01 to 100 milligrams per kilogram of body weight. Ordinarily 1 to 5, and preferably 1 to 10 milligrams per kilogram per day given in divided doses 1 to 6 times a day or in sustained release form, may be effective to obtain desired results.

The immunogen can be incorporated into pharmaceutical compositions suitable for administration to a subject. For example, the pharmaceutical composition may comprise an immunogen and a pharmaceutically acceptable carrier. As used herein, "pharmaceutically acceptable carrier" includes solvents, dispersion media, coatings, antibacterial and antifungal agents, isotonic and absorption delaying agents, and the like that are physiologically compatible. Examples of pharmaceutically acceptable carriers include one or more of the following: water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibodies of the present invention.

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies.

Therapeutic compositions typically are sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody or antibody fragment) in the required amount in an appropriate solvent with one or a combination of ingredients enumerated above, as required, followed by sterile filtration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yield a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art (see, e.g., Sustained and Controlled Release Drug Delivery Systems, J. R. Robinson. ed., Marcel Dekker, Inc., New York, 1978).

The pharmaceutical compositions of the invention may include a "therapeutically effective amount" or a "prophylactically effective amount" of an immunogen. A "therapeutically effective amount" refers to an amount effective, at dosages and for periods of time necessary, to achieve the desired therapeutic result. A therapeutically effective amount of the antibody or antibody fragment may vary according to factors such as the disease state, age, sex, and weight of the individual, and the ability of the antibody or antibody fragment to elicit a desired response in the individual. A therapeutically effective amount is also one in which any toxic or detrimental effects of the antibody or antibody fragment are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims.

As used herein the singular forms "a", "and", and "the" include plural referents unless the context clearly dictates otherwise. All technical and scientific terms used herein have the same meaning as commonly understood to one of ordinary skill in the art to which this invention belongs unless clearly indicated otherwise.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

All publications and patent applications cited in this specification are herein incorporated by reference as if each individual publication or patent application were specifically and individually indicated to be incorporated by reference.

EXPERIMENTAL

Example 1

The following examples are provided in order to demonstrate and further illustrate certain preferred embodiments and aspects of the present invention and are not to be construed as limiting the scope thereof.

In the experimental disclosure which follows, the following abbreviations apply: M (molar); mM (millimolar); nM (nanomolar); pM (picomolar); mg (milligrams); μg (micrograms); pg (picograms); ml (milliliters); μl (microliters); ° C. (degrees Celsius); OD (optical density); nm (nanometer); BSA (bovine serum albumin); and PBS (phosphate-buffered saline solution).

Patients with advanced follicular lymphomas (FL) are incurable with currently available therapies. Nevertheless, survival of these patients has improved in the past decade with the introduction of rituximab immunotherapy. As with rituximab, immunological targeting of the unique portions of their tumor surface immunoglobulins, or idiotype (Id), can be achieved by infusion of patient specific monoclonal antibodies generated after immunization of mice with Id proteins. In contrast with this passive approach for immunological targeting of idiotypes, direct immunization of patients with their own Id proteins has theoretical and practical advantages for generation of active responses. These surface immunoglobulin molecules contain a potentially immunogenic portion termed the idiotype (Id), comprising tumor specific molecular determinants that are unique to each patient. Id proteins from each tumor can be "rescued" by hybridoma technology or produced by recombinant methods and formulated into patient-specific active immunotherapy, capable of inducing both humoral and cell mediated immune responses in patients against their own tumor cells.

Idiotype proteins can be made more immunogenic by chemical coupling to keyhole limpet hemocyanin (KLH), a protein from the marine snail *Megathura crenulata*. The immune response to injected Id-KLH can be further enhanced by co-injecting GM-CSF, which functions as an immunological adjuvant. In phase II trials, patients mounting anti-Id humoral immune responses had longer freedom from progression and improved survival compared to patients who did not mount such responses.

These phase II results motivated the current randomized, multi-center study designed to compare the clinical outcome of FL patients after chemotherapy who received a specific immunotherapy consisting of a patient-specific recombinant Id coupled to KLH (MyVax®) (Timmerman et al., 2009) and co-administered with GM-CSF, versus a control immunotherapy consisting of KLH plus GM-CSF.

Material and Methods:

Patients: This randomized, blinded Phase 3 trial was conducted at 32 centers in Canada and the United States, and registered as NCT00017290 at ClinicalTrials.gov. All patients signed an informed consent and the study was approved by the institutional review boards or ethics committees at each center. Eligible patients were at least 18 years of age with untreated follicular lymphoma (FL) requiring therapy, had Ann Arbor stage III or IV disease, and included World Health Organization histological grades 1, 2, or 3 (Jaffe and World Health Organization, 2001) (IWF groups B, C, D were considered equivalent). The diagnosis of FL was confirmed by central pathology review of a lymph node biopsy, which was concordant for grade in 67% of cases. Patients had ECOG performance scores of 0, 1 or 2. Exclusion criteria included serological evidence for exposure to HIV, hepatitis B and hepatitis C, history of autoimmune disease or conditions requiring treatment with immunosuppressive agents including corticosteroids within 12 months of chemotherapy, pregnancy, and/or breastfeeding. Patients with prior malignancy other than basal cell carcinoma of the skin or cervical carcinoma in situ were excluded. Patients had a computed tomography (CT) scan of the chest, abdomen and pelvis and submitted a tumor tissue sample for MyVax® manufacturing prior to initiation of chemotherapy. MyVax® was manufactured for all randomized patients including those assigned to receive control immunotherapy.

Patients received CVP chemotherapy every 21 days for 8 cycles, wherein Cyclophosphamide (1000 mg/m$^2$) and Vincristine (1.4 mg/m$^2$, individual centers were allowed to choose to cap vincristine at 2.0 mg or give the full calculated dose) were given intravenously and Prednisone (100 mg/day×5 days) was given orally. Patients were restaged between 4 weeks and 8 weeks after the first day of the eighth cycle of CVP with physical examination and CT scans of the chest, abdomen, and pelvis. If scanned previously, a CT scan of the neck was repeated. In order to assign an overall clinical disease response status of complete response (CR) or complete response unconfirmed (CRu), a bone marrow biopsy was repeated in those patients whose bone marrows were histologically positive (or indeterminate) prior to chemotherapy. All scans performed through the 2-year follow-up post-immunization were centrally reviewed.

Study Design: Patients achieving at least a PR following 8 cycles of CVP were restaged 22 weeks after start of therapy. This time-point was selected based on results from pre-clinical and earlier clinical studies of idiotypic vaccination revealing improved immune responses with lower disease burden, the kinetics of typical responses to CVP chemotherapy, and the time required for vaccine manufacture. Response was confirmed by central radiographic review. Patients with at least a PR were randomized (2:1) to MyVax® or control immunotherapy stratifying by investigational site and baseline disease status (CRu/PR versus CR). MyVax® was manufactured for all randomized patients. Upon randomization, an un-blinded statistician at ICON Clinical Research instructed an un-blinded individual at Genitope Corporation whether to provide a patient's MyVax® or the control immunotherapy. All other personnel at Genitope Corporation, ICON Clinical Research and the study sites were blinded to treatment.

Manufacture of MyVax® and Control Immunotherapies: Total RNA was isolated from tumor biopsies using TriZOL and/or RNeasy Midi Kits (Qiagen, Valencia, Calif.), and first strand cDNA amplified with primers specific for the appropriate heavy chain or light chains as determined by flow cytometry. Reverse transcription and polymerase chain reaction (RT-PCR) were performed using family-specific Ig variable and constant region primers located 5' to those used for cDNA synthesis, with a separate reaction for each V region family. DNA from individual PCR reactions was directly sequenced, then confirmed by repeat RT-PCR. Each patient's Id-encoding complementary DNA was subcloned into plasmid expression vectors containing an IgG3 heavy chain constant region sequence and the light chain constant region sequence matching that of the tumor. The IgG3 constant region was chosen to allow a uniform manufacturing process and humoral immune response testing of the major IgG isotypes. Individual clones were isolated and sequenced, and those matching the original RT-PCR product selected for expression in mammalian cells. Plasmids each directing the expression of the Id, the selectable marker hypoxanthine-guanine phosphoribosyl transferase (HG-PRT), and the amplifiable marker dihydrofolate reductase (DHFR) were co-electroporated into the BW5147.G.1.4 a murine lymphoma cell line, followed by selection in azaserine and hypoxanthine. Selected clones were assayed for Ig production by ELISA, and high-expressing clones grown further in methotrexate to amplify the Ig genes until secretion level was adequate for large-scale production. Production cell lines were incubated in HyQ CCM-1 media (Hyclone, Logan, Utah) in cell culture bags (Medtronic, Chicago, Ill.) at 37° C. for 8 to 12 days. Id was purified from supernatants using HiTrap Protein G columns (GE Healthcare, Newark, N.J.), eluting with 100 mM glycine, pH 2.7 and then dialyzed into normal saline. Each patient's Id was conjugated to KLH (Biosyn, Carlsbad, Calif.) with 0.1% glutaraldehyde (Sigma, St. Louis, Mo.) at room temperature for 60 minutes and then dialyzed into normal saline and stored at −80° C. The conjugations were performed at 0.5 mg/ml each of Id and KLH. For the control immunotherapy, KLH was self-conjugated (KLH-KLH) at 0.5 mg/ml using the same conditions. The final products, Id-KLH and KLH-KLH, were tested for sterility and endotoxin.

Immunization: The dosing schedule was a series of 7 subcutaneous (SC) immunizations with 1.0 mg Id-KLH (MyVax®) or 0.5 mg KLH-KLH (control) at 4-week intervals over a period of 24 weeks. Each dose was split evenly between 2 sites injected bilaterally in the anterior thigh superficially to the quadriceps muscle of each leg. Each series of MyVax® immunizations consisted of Id-KLH immunization followed by 250 µg granulocyte-macrophage colony stimulating factor (GM-CSF) split between the 2 injection sites. Each series of control immunotherapy immunizations consisted of KLH-KLH immunization followed by 250 µg granulocyte-macrophage colony stimulating factor (GM-CSF) split between the 2 injection sites. On Days 2-4 of each immunization series, GM-CSF alone (250 µg total dose divided equally between the 2 injection sites) was injected SC at the original injection sites.

Immune Response Testing: Sera were collected from patients immediately prior to immunizations #1, #3, #4, #5, #6 and #7, then, 2 to 4 weeks, 3 months, 6 months, 9 months and 12 months following $7^{th}$ (or last) immunization. Serum collection was discontinued after disease progression. Anti-idiotype and anti-KLH ELISAs were performed on all study subjects across both arms of the study. All sera were coded prior to testing so that personnel performing the immune response testing were blinded to patient identity. Criteria for calling a patient serum immune response positive or negative were pre-specified, with those receiving at least 4 immunizations considered evaluable for immune response. A positive anti-Id IR was pre-defined as post-immunization serum with a mean absorbance value greater than the mean absorbance value of pre-immunization serum plus two standard deviations from the mean absorbance of the replicate wells at 4-fold lesser dilution. A positive anti-KLH IR is defined as post-immunization serum with a titer ≥1 µg/ml above pre-immunization serum titer plus two standard deviations from the mean absorbance of the replicate wells at that dilution. For both assays, positive post-immunization sera were required to demonstrate a measurable titer with the mean absorbance value of a 4-fold dilution decreasing by at least two fold. Peak titers were assessed from serially collected sera up to the $7^{th}$ immunization.

Anti-Idiotype ELISA:

96-well plates were coated with a patient's specific idiotype protein or idiotype protein from a patient for whom a chimeric anti-Id monoclonal antibody (mAb) was created as the control. After washing the plates, dilutions of the chimeric mAb specific for control idiotype were added alongside baseline and post-vaccine sera to the appropriate control wells and dilutions of the appropriate patient sera are added to the appropriate test wells, with baseline serum and appropriate positive and negative controls on every plate. Wells for a negative control and positive controls were on every plate. Plates were incubated, then washed and a cocktail of biotinylated anti-human IgG1, IgG2 and IgG4 were added. Following incubation, the plates were washed and streptavidin-HRP was added. The plates were incubated then washed. The colorimetric substrate TMB was added and the plates were read in a plate reader. An anti-Id titer was determined by referencing the standard curve.

Anti-KLH ELISA:

96-well plates were coated with KLH protein. After washing the plates, dilutions of a reference standard anti-KLH serum with defined activity pooled from patients with high titer anti-KLH responses and dilutions of patient sera were added to the appropriate wells. Baseline serum was used on every plate. Wells for a negative control and positive controls were on every plate. Plates were incubated and then washed and a cocktail of biotinylated anti-human IgG1, IgG2, and IgG4 were added. Following incubation, the plates were washed and streptavidin-HRP was added. The plates were incubated then washed. The colorimetric substrate TMB was added and the plates were read in a plate reader. An anti-KLH titer was determined by referencing a standard curve.

Analysis of Endpoints & Statistical Methods: Patients were assessed for clinical response by CT scans and physical exam (PE) following immunizations no sooner than 2 weeks and no later than 4 weeks after the completion of the $7^{th}$ immunization series using standard criteria. Patients were evaluated by PE at months 3, 6, 9, 12, 18 and 24 following the completion of immunization series #7 or any other time clinically indicated. Patients were evaluated by CT scans at months 6, 12, 18 and 24 following the completion of immunization series #7. Survival status and course of disease data were collected from randomized patients every 6 months from the date of randomization. The primary end point was progression free survival (PFS), defined as time from randomization to the earliest time point identifying progression or death from any cause. Progressions during the first 30 months following randomization were determined by central radiographic review, and later progressions were determined by the local investigators. Response improvements were noted by comparing CT scans at randomization with scans from the scans performed at 2 years post-immunization. Patients who received subsequent anti-lymphoma therapy (SALT) before disease progression was noted by central review were censored on the first date of SALT. Secondary efficacy endpoints analyzed included SALT-free survival (SALT-FS, defined as time from randomization to SALT or death from lymphoma), clinical response improvement after immunization, overall survival, and comparisons between different Follicular Lymphoma International Prognostic Index (FLIPI) risk groups. Despite significant variability among physicians in selecting secondary therapies for FL, all clinicians involved in decisions for SALT remained blinded to treatment arm assignments.

Analyses of PFS and SALT-FS were conducted using the log-rank test with the results expressed as Kaplan-Meier plots. A Cox proportional hazards analysis of PFS was conducted including the demographic and baseline characteristics. P-values from statistical tests were 2-sided. Based on predetermined criteria, the trial was un-blinded when all patients completed the evaluation at 2 years post-immunization. The trial design assumed a median PFS of 22 months from randomization for the control and 43 months from randomization for the experimental group with accrual duration of 15 months. The actual accrual duration was 42 months for the entire cohort. Using a two-sided log-rank test at significance level of 0.01, the trial had a power of 96% to detect a 21 month difference and at least 80% power to detect a 14 or more month difference between the two groups.

The relationship of humoral IRs to MyVax® and KLH as continuous variables was assessed using univariate Cox proportional-hazards analysis, with PFS as the dependent variable. Using the coxph function in the R statistical package, the Wald test was used to assess the significance of each covariate, represented by the base-10 logarithms of the maximal observed titer against MyVax® or KLH for any given patient.

Results:

This randomized, blinded Phase 3 trial (NCT00017290) was conducted at 32 centers in North America. Among 513 enrolled patients who met initial screening criteria, 226 patients who started chemotherapy either failed to achieve at least a partial response or progressed prior to randomization (FIG. 1). After 8 cycles of chemotherapy and a ~6 month rest period, the remaining 287 patients were randomly assigned to either receive MyVax® or control immunotherapy on a 2:1 basis, and this group was evaluable for clinical outcome as the intent to treat population. The characteristics of the randomized patients were well balanced between the two arms (Table 1). The first patient was screened in November 2000 and started immunization in November 2001, while the last patient starting immunization in June 2005. The database was locked and the trial was un-blinded in December 2007 after all patients completed the evaluation at two years post-immunization as pre-specified.

| Characteristic | MyVax ® no. (%) | Control Immunotherapy no. (%) |
| --- | --- | --- |
| Number of Patients | 192 | 95 |
| Age | | |
| Younger than 40 years | 26 (13.5%) | 15 (15.8%) |
| 40 to 50 years | 60 (31.3%) | 33 (34.7%) |
| 50 to 60 years | 56 (29.2%) | 25 (26.3%) |
| 60 years or older | 50 (26.0%) | 23 (24.2%) |
| Range (years) | 22 to 80 | 25 to 80 |
| Median (years) | 50 | 50 |
| Sex | | |
| Female | 106 (55.2%) | 51 (53.7%) |
| Male | 86 (44.8%) | 44 (46.3%) |
| ECOG Performance Status | | |
| 0 | 135 (70.3%) | 66 (69.5%) |
| 1 | 55 (28.6%) | 27 (28.4%) |
| Not evaluable/missing | 2 (1.1%) | 2 (2.1%) |
| Histological Grade (WHO) Local Review | | |
| Grade 1 | 111 (57.8%) | 59 (62.1%) |
| Grade 2 | 68 (35.4%) | 31 (32.6%) |
| Grade 3 | 12 (6.3%) | 5 (5.3%) |
| Not evaluable/missing | 1 (0.5%) | |
| Central Review | | |
| Grade 1 | 97 (50.5%) | 49 (51.6%) |
| Grade 2 | 75 (39.1%) | 37 (38.9%) |
| Grade 3 | 13 (6.8%) | 7 (7.4%) |
| Not evaluable/missing | 7 (3.6%) | 2 (2.1%) |
| Stage (Ann Arbor) | | |
| III | 80 (41.7%) | 36 (37.9%) |
| IV | 112 (58.3%) | 59 (62.1%) |
| Risk Group (FLIPI) | | |
| Low Risk | 23 (12.0%) | 6 (6.3%) |
| Intermediate Risk | 100 (52.1%) | 53 (55.8%) |
| High Risk | 67 (34.9%) | 36 (37.9%) |
| Not evaluable/missing | 2 (1.0%) | 0 (0%) |
| Bone marrow involvement | 128 (66.7%) | 66 (69.5%) |
| B-Symptoms | 31 (16.1%) | 17 (17.9%) |
| Bulky disease | 57 (29.7%) | 16 (16.8%) |
| Elevated LDH | 29 (15.1%) | 17 (17.9%) |
| One or more extranodal sites | 53 (27.6%) | 25 (26.3%) |
| Duration of watchful waiting (Median, days) | 100 | 98 |

Although randomized patients were not stratified based on their prognostic risk group defined by FLIPI score, there was a similar distribution of patients between the two arms, including those with intermediate risk or high risk features (Table 1).

Figure 2:
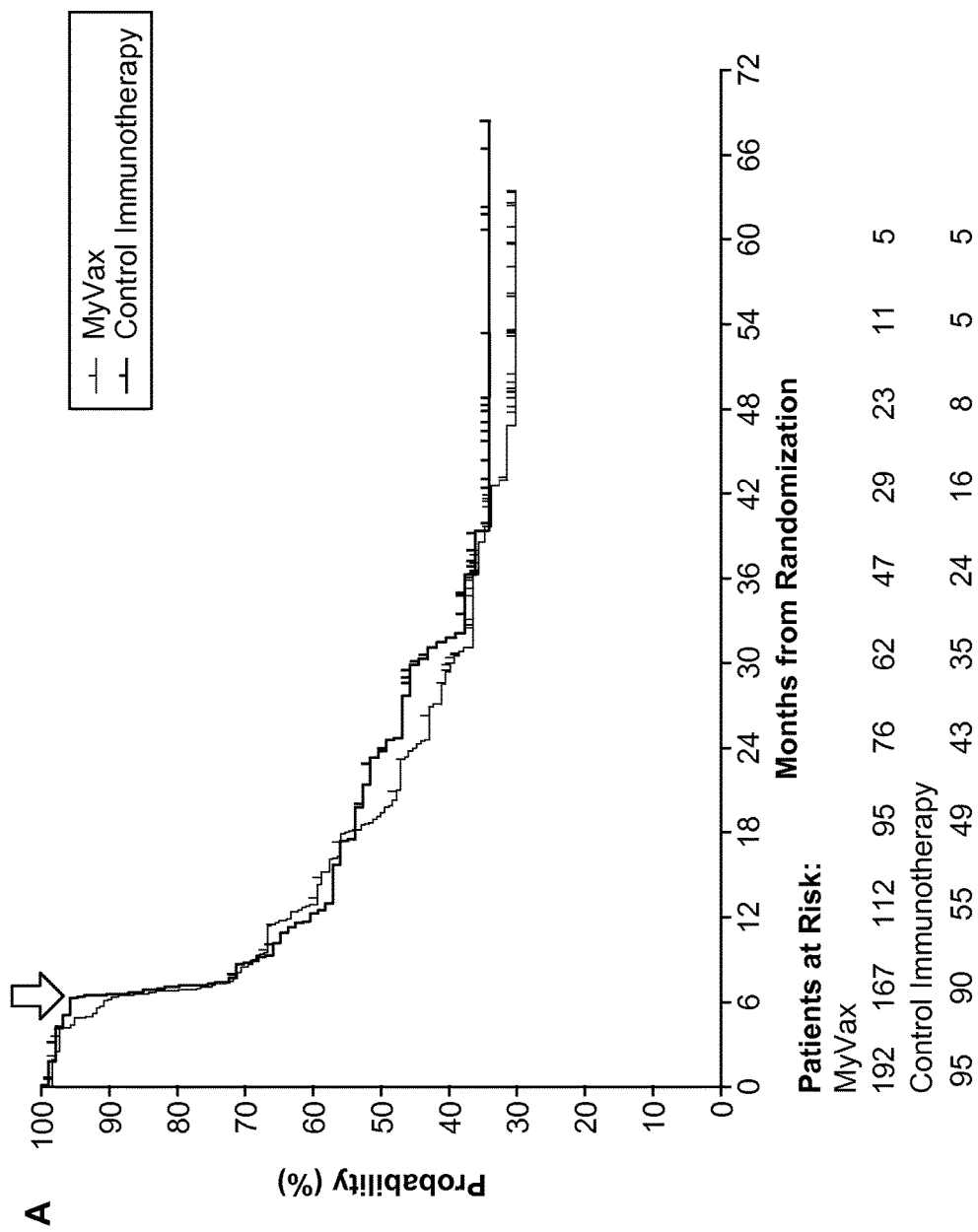
FIG. 2: Comparison of treatment arms for the study's primary end-point, Progression Free Survival (PFS) [Panel A], and for a pre-specified secondary end-point, time to Subsequent Anti-Lymphoma Therapy (SALT) [Panel B]. Depicted Kaplan-Meier curves capture patients randomized to MyVax versus Control Immunotherapy, with corresponding end-points measured from time of randomization for the intent-to-treat population (n=287). The arrow-head (Panel A) reflects timing of the first radiographic response assessment. SALT was administered in administered in blinded fashion. Neither endpoint was significantly different between study arms. Panel C depicts comparison of SALT and PFS for the entire randomized population, reflecting the average delay between disease progression and institution of second-line therapies on clinical grounds. Similar outcomes were observed among FLIPI prognostic risk groups.

PFS and Subsequent therapy. There was no statistically significant difference in the PFS of entire group of patients receiving MyVax® compared to patients in the control immunotherapy arm (FIG. 2A). Notably, an apparent plateau was observed for PFS of >30% at 4 years on the Kaplan-Meier curves for both arms, though likely influenced by the requirement for durable response to chemotherapy preceding vaccination. Among patients achieving confirmed or unconfirmed complete remissions prior to vaccination, PFS was not significantly different between arms. After a median follow-up of 48 months post-chemotherapy, 49.5% of the patients in this trial had not received subsequent anti-lymphoma therapy. There was also no difference in the time to subsequent anti-lymphoma therapy (SALT), a pre-specified secondary endpoint, between the two arms of the trial (FIG. 2B). Patients in both arms had a significant time interval between time of radiographic disease progression and time of SALT (FIG. 2C).

Figure 3:
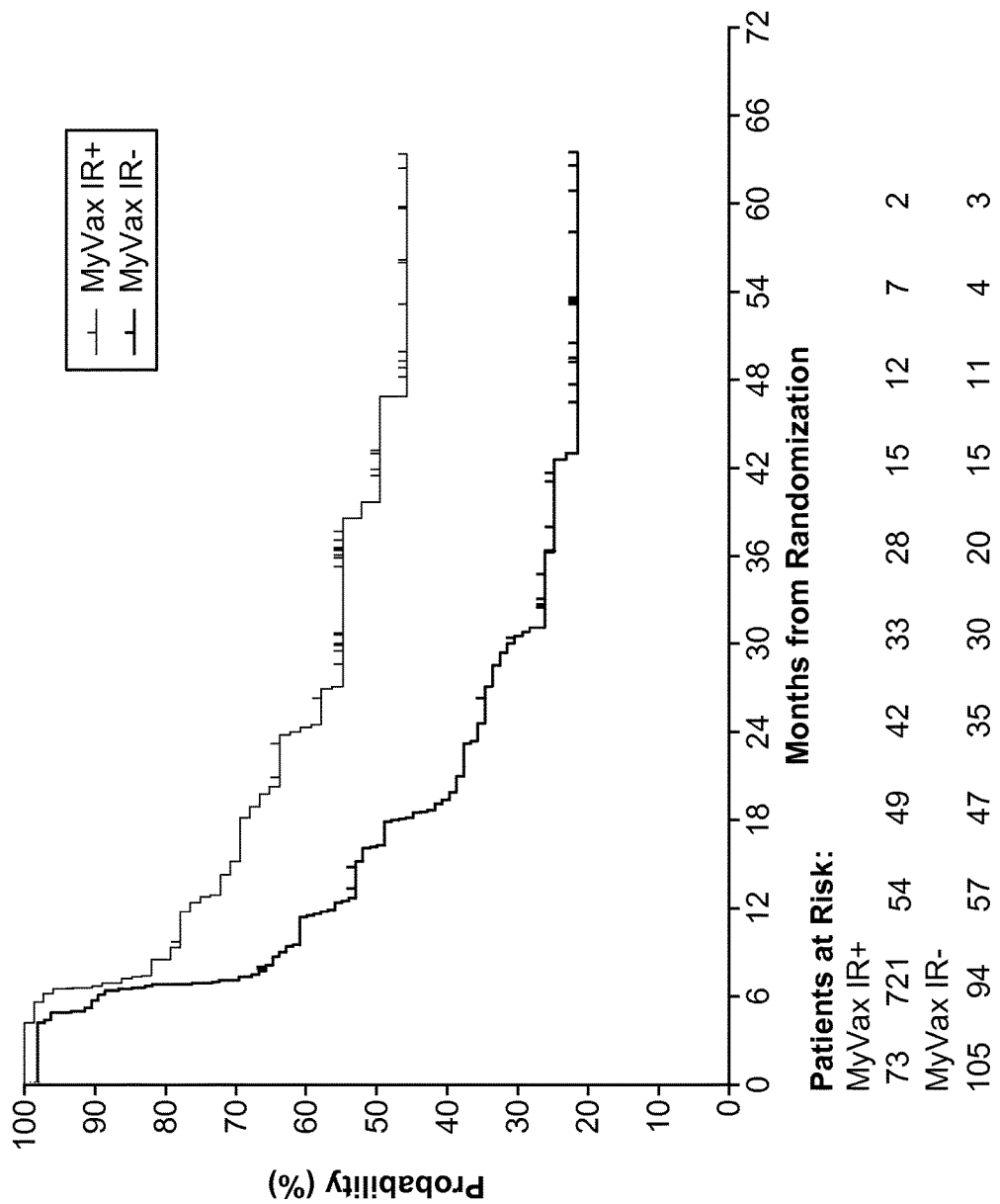
FIG. 3: Superior outcomes among patients mounting humoral immune response to idiotypic vaccination. Patients randomized receiving MyVax were assessed for anti-idiotypic antibody responses, and stratified into "IR+" and "IR−" designations based on pre-specified criteria considering serial serological assessments as detailed within methods. Kaplan-Meier strata distinguish superior Progression Free Survival (PFS) of IR+ vs IR− patients treated with MyVax.

Among patients receiving MyVax® that were evaluable for IR using pre-defined criteria, 41% were classified as mounting significant anti-Id antibody responses (IR+), while 59% were considered negative for such responses (IR−). Patients classified as IR+ MyVax® patients had a highly significant improvement in PFS compared to IR− patients (FIG. 3), as reflected in the disparity between the median PFS for the two groups.

Figure 4:
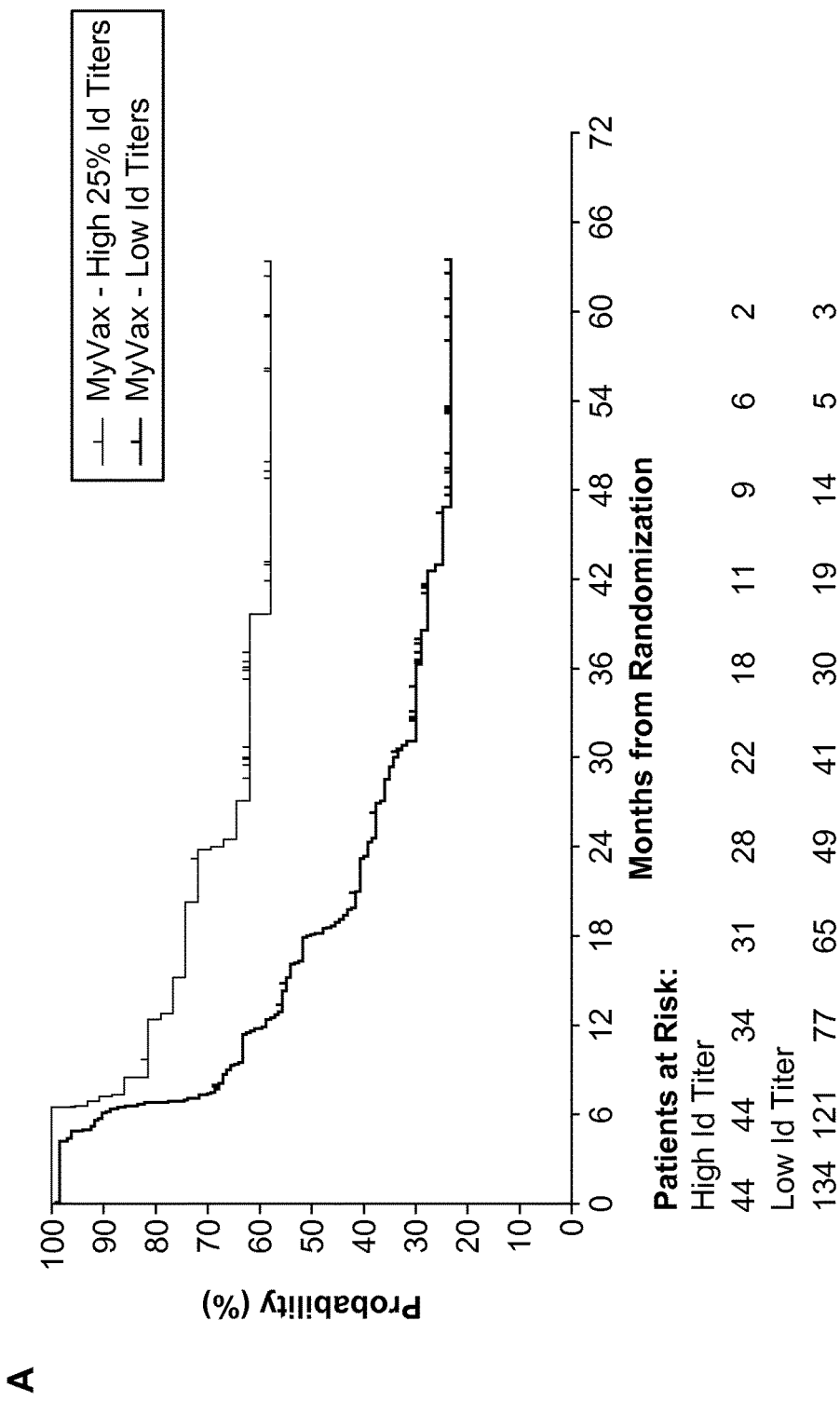
FIG. 4: Humoral immune responses against MyVax and KLH. (A) Comparison of patients within the top 25th percentile of maximal anti-Id titers versus those within bottom 75th percentile. (B) Similar distribution of peak titers of anti-idiotype and anti-KLH Titers in the randomized cohort. (C) Among patients receiving MyVax, those with highest anti-KLH titers (top quartile) exhibit superior PFS when compared with the lowest titers (bottom 75-% ile). (D) PFS of patients receiving Control Immunotherapy, when stratified exactly as in (C). Similar results were obtained when comparing patients with peak anti-KLH responses within the lowest quartile to those within the top three quartiles.

Both anti-Id and anti-KLH immune responses were measured quantitatively. As with the pre-specified categorical assessments of anti-Id IR, when assessed quantitatively, there was a significant graded relationship between magnitude of peak anti-Id IR and PFS. Specifically, the PFS of the patients with the highest peak anti-Id titers was superior to the remaining MyVax® patients (FIG. 4A). In contrast with anti-Id IR, all but one patient receiving MyVax® progressing after 4 immunizations mounted an anti-KLH IR. The MyVax® and control patients show a very similar distribution of peak anti-KLH titers (FIG. 4B). As with the distinct outcomes of MyVax® patients observed when stratified by peak anti-Id IR (FIG. 4A), the subset within the top quartile of peak anti-KLH titers has superior PFS when compared to the remaining patients (FIG. 4C). In contrast, the PFS of the 25% of control immunotherapy patients with the highest anti-KLH titers was not statistically different from the remaining 69 patients (FIG. 4D). In a similar analysis focusing on patients with smallest anti-KLH responses within the MyVax® arm, those within the lowest quartile of peak anti-KLH titers had significantly worse PFS than the remaining patients. Once again, in the control immunotherapy arm, the PFS of patients in the corresponding lowest quartile of anti-KLH titers was not statistically different from the remaining patients. The PFS of the 25% of MyVax® patients with the lowest peak anti-KLH titers was also significantly worse than control immunotherapy patients.

A major factor influencing the study's negative results for its primary endpoint may relate to the selective benefit of MyVax® to a subset of patients capable of mounting humoral responses against both MyVax® and KLH. Here, the current study examined the relationship between pre-specified humoral immune responses (IR) and clinical outcomes, based on prior pre-clinical and phase 2 clinical data providing a strong rationale for prospectively testing such associations. Notably, within the MyVax® arm, patients mounting anti-Id immune responses had a significantly superior PFS when compared to patients without such responses or to patients in the control arm. This result replicates observations from previous phase 2 trials, confirming that patients with stronger IRs have better outcomes, and is consistent with the well established principle in infectious disease vaccination that higher titer responses are more protective.

The discovery and validation of additional and novel biomarkers of immunological and clinical responses is critical for identifying patients likely to benefit from such therapy, ideally preceding vaccination. Candidate biomarkers that might be predictive of IR and therapeutic benefit could include gene expression signatures of tumors, host genotypes, and specific idiotypic features of tumors. Furthermore, as T cells can mediate significant anti-tumor immune responses against diverse tumors including follicular lymphomas, by prospectively profiling effector T-cell responses, future studies might capture important additional aspects of host immunity for defining populations benefiting from autologous vaccination with idiotype vaccines.

Example 2

Patient groups were analyzed for features that distinguish between responder and on-responder groups as described above. Non-significant differences were attributed to Ig heavy chain isotype (IgM, G, A); Ig light chain isotype (Igκ, Igλ); IgH V-gene repertoire (VH family); IgH J-gene repertoire (JH family); somatic mutation frequency; antigen selection inference; Hep2 Reactivity and pattern. Significant differences were found in the CDR3 length, and in the H1/L1 tyrosine frequency.

Figure 5A:
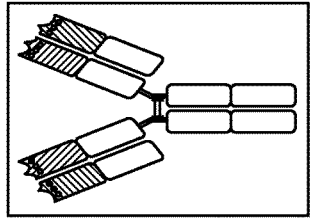
FIG. 5A The frequency of tyrosines in CDR1 of both heavy and light chains is highly significantly associated with immune response. Using the idiotypic cDNA sequences derived from lymphoma biopsies, immunoglobulin sequences from the light and heavy chain genes were analyzed using IMGT VQUEST, and variable regions partitioned into seven structurally defined regions depicted in columns (Framework regions 1 through 4 [FR1/2/3/4], and Complementarity Determining Regions 1 through 3 [CDR1/2/3]). For each of the 20 amino acids (rows), its frequency was enumerated across these seven structurally defined regions in each patient's idiotypic sequence, considering the full patient-derived idiotypic vaccine sequence (combining the heavy and light genes; right group), or when the light and heavy chain genes were considered separately (left and middle groups). Individual amino acids were then assessed for differential distribution among patients mounting immune responses (Id-R) or failing to mount them (Id-NR), with statistical significance estimated using a Student's t-test and depicted as gradations of color corresponding to the negative logarithm of p-values within the table and inset key (right). Tyrosine (Y) frequency in CDR1 exhibited the largest and most significant difference between the Id-R and Id-NR patient idiotypes (uncorrected p=0.00008, Bonferroni corrected p=0.01) when considering the combined MyVax protein FIG. 5B. When considering the heavy and light genes separately, the frequency of tyrosines in CDR1 of both chains was also significantly associated with immune response (left and middle panels), with a magnitude smaller than the combined protein. Such interaction between the tyrosine content of unique patient specific heavy-light pairings suggests a co-dominant effect, where an excess within either heavy or light chain can be associated with immune responses.
Figure 5B:
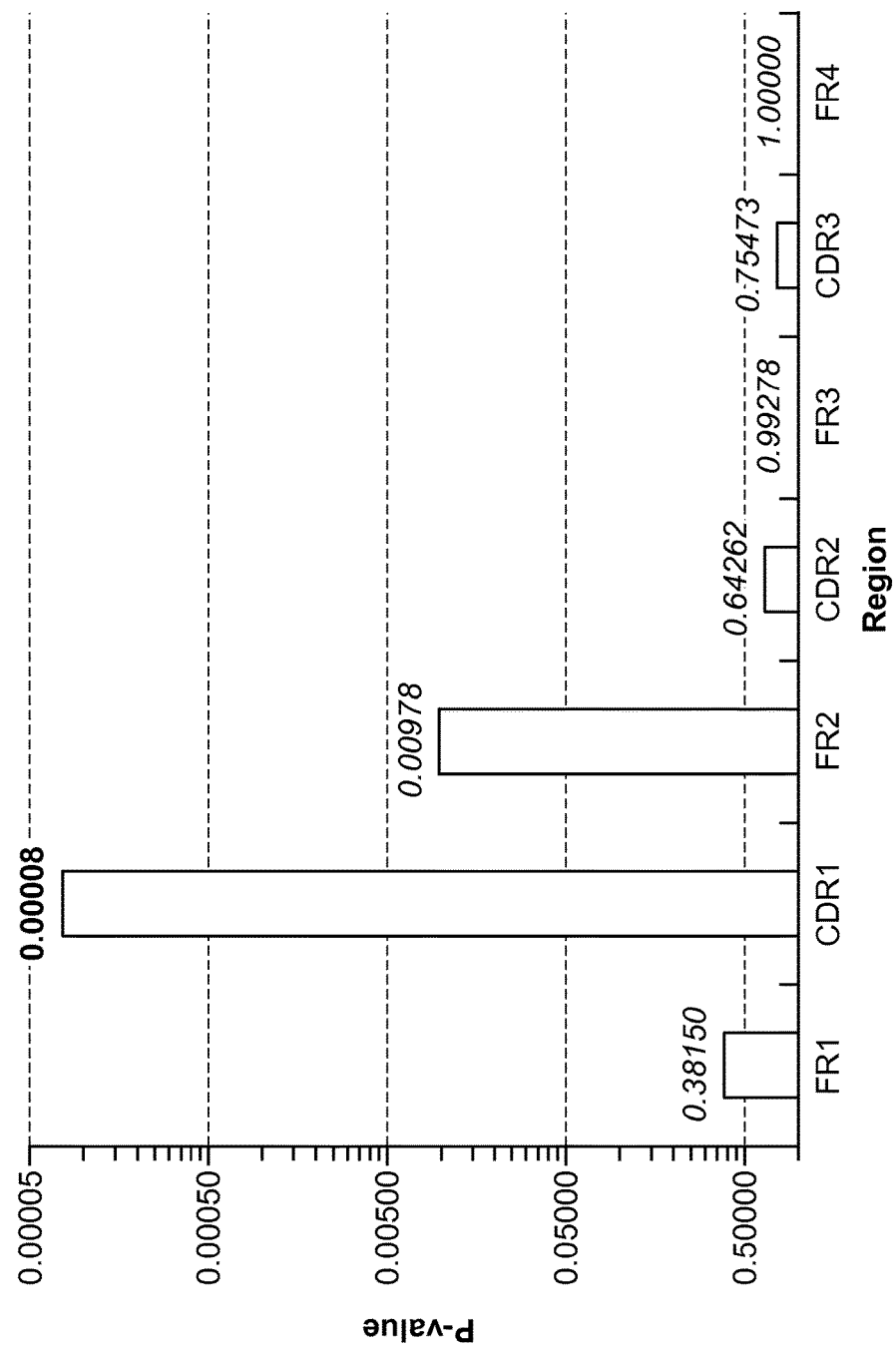

Amino acids were enumerated across the seven topographically constrained regions in each patient's idiotypic sequence; considering the tumor's unique immunoglobulin heavy and light chain genes. These regions are termed Framework regions 1 through 4 [FR1/2/3/4], and Complementarity Determining Regions 1 through 3 [CDR1/2/3]. It was determined whether any sequence features were differentially distributed among patients mounting immune responses (Id-R) or failing to mount them (Id-NR). The tyrosine frequency emerged as a dominant finding, and it was found that the frequency of tyrosines in CDR1 of both heavy and light chains is highly significantly associated with immune response (FIG. 5). There is a significant co-dominant effect (p<0.01) between the heavy and light chains such that an excess within either heavy or light chain contributes to poor immune responses.

Figures 6A, 6B:
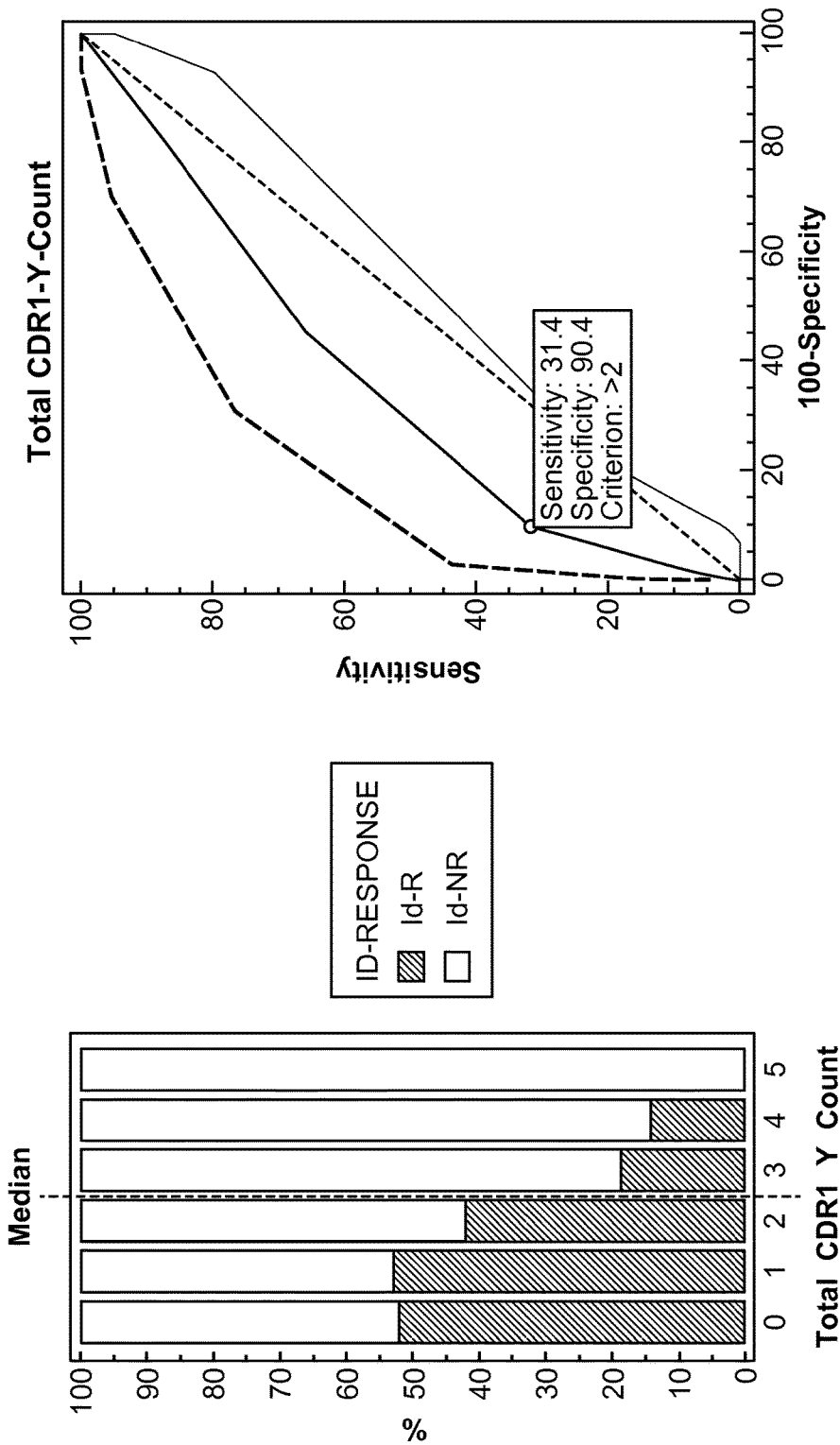
FIG. 6. Higher CDR1 tyrosine frequency is associated with a lower likelihood of anti-Id humoral immune response. (A) The total number of tyrosines within the CDR1 region of MyVax idiotype vaccines and comprising the corresponding heavy and light chain regions (X-axis) is inversely related to the probability of mounting a significant humoral immune response using pre-specified criteria (Id-R, Y-axis). The dotted line represents the median number (n=2) of tyrosines enumerated in the combined CDR1 of 707 patients with Non-Hodgkin's lymphomas. (B) Receiver-Operator Curve (ROC) curve analysis assessing performance of CDR1 tyrosine frequency as a predictor of immune response. The associated Area Under Curve (AUC) was 0.64, with the optimal threshold (>2 tyrosines in CDR1 distinguishing CDR1-$Y^{hi}$ from CDR1-$Y^{lo}$) having 90.4% specificity for correctly predicting lack of immune response (Id-NR).

The number of tyrosines within CDR1 of heavy and light chains is continuously associated with probability of mounting a significant humoral immune response using pre-specified criteria (FIG. 6A), with the magnitude of these immune response, as well as with Progression Free Survival (PFS) in a univariate Cox regression (FIG. 6, P<0.01).

While the continuous relationships between the tyrosine count of CDR1 in heavy and light chains are biologically compelling, a clinical decision tool beneficially provides a discrete threshold. Therefore, for each patient, a threshold of 3 or more tyrosines in aggregate (when considering CDR1 of their Heavy and Light chains) was determined to predict lack of a humoral immune response. This threshold is selected relative to the median number of tyrosines (n=2) observed in the CDR1 regions of the paired heavy and light chain idiotypes across a large cohort of patients (n=707) with lymphoma (FIG. 6A). Consistent with these thresholds, when combining the heavy and light chain CDR1 Y count and applying Receiver Operator Curve analyses, more than 2 tyrosines in CDR1 (for discriminating CDR1-$Y^{hi}$ from CDR1-$Y^{lo}$) had the best performance in predicting immune response (FIG. 6B).

Figure 7B:
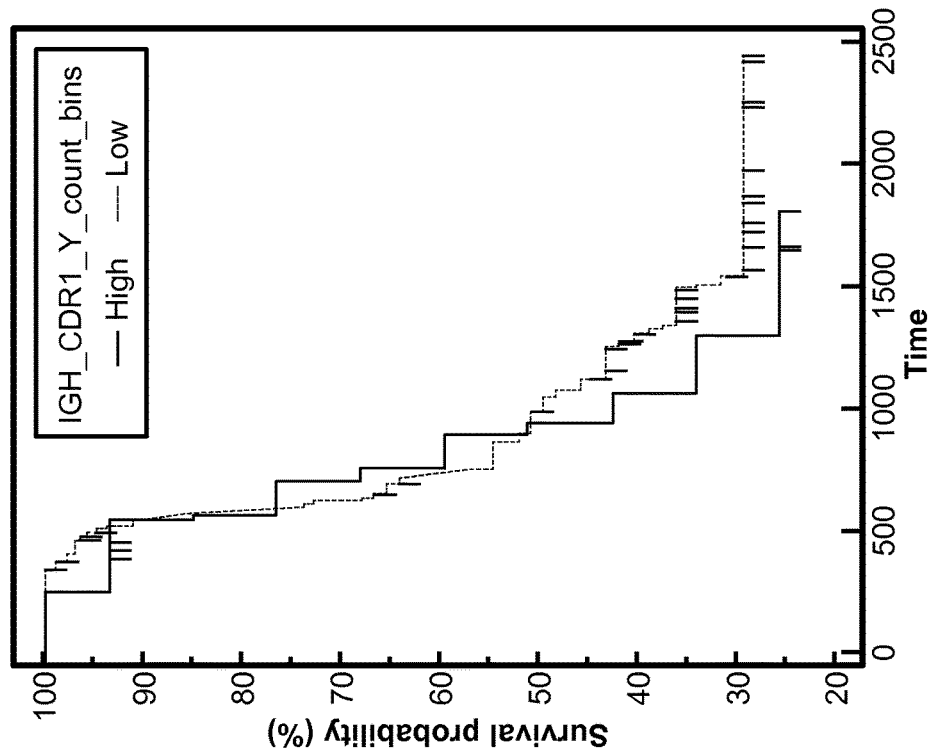
FIG. 7: (A) Higher CDR1 tyrosine frequency is associated with inferior progression-free survival (PFS) among patients receiving MyVax. Kaplan-Meier curves depict patients stratified by CDR1 tyrosine count (CDR1-$Y^{hi}$ from CDR1-$Y^{lo}$ as defined in FIG. 6), with the log-rank test used to test significance of separation (P<0.0001, Hazard ratio 2.47, 95% Confidence Interval 1.50-4.06). X-axis represents time from registration, and Y-axis represents Progression Free Survival. (B) Among patients receiving control immunotherapy, CDR1 tyrosine frequency is not significantly associated with PFS.
Figure 7A:
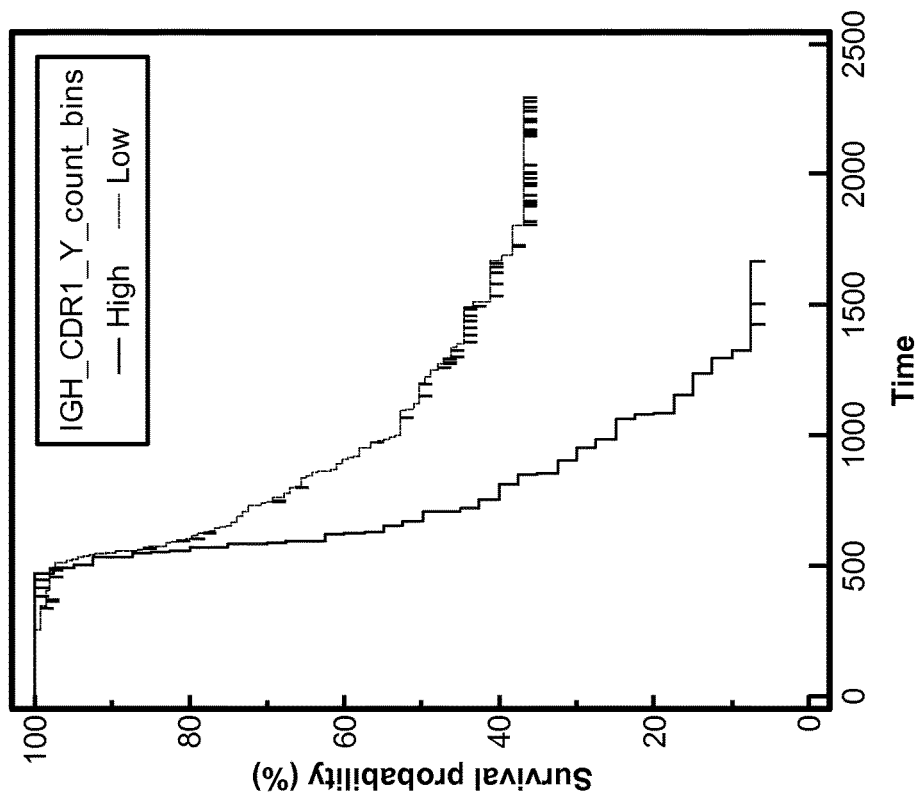

The tyrosine-count is thus predictive of clinical benefit conferred by the active immunization, and not simply a prognostic biomarker serving as a proxy for underlying heterogeneity among tumors, supported by a lack of association between this tyrosine frequency and known factors influencing outcomes of patients with follicular lymphoma, including histological grade, and the Follicular Lymphoma International Prognostic Index [FLIPI]. Specifically, among patients receiving control immunotherapy, CDR1 tyrosine frequency was not associated with outcomes (FIG. 7B)

Figure 8:
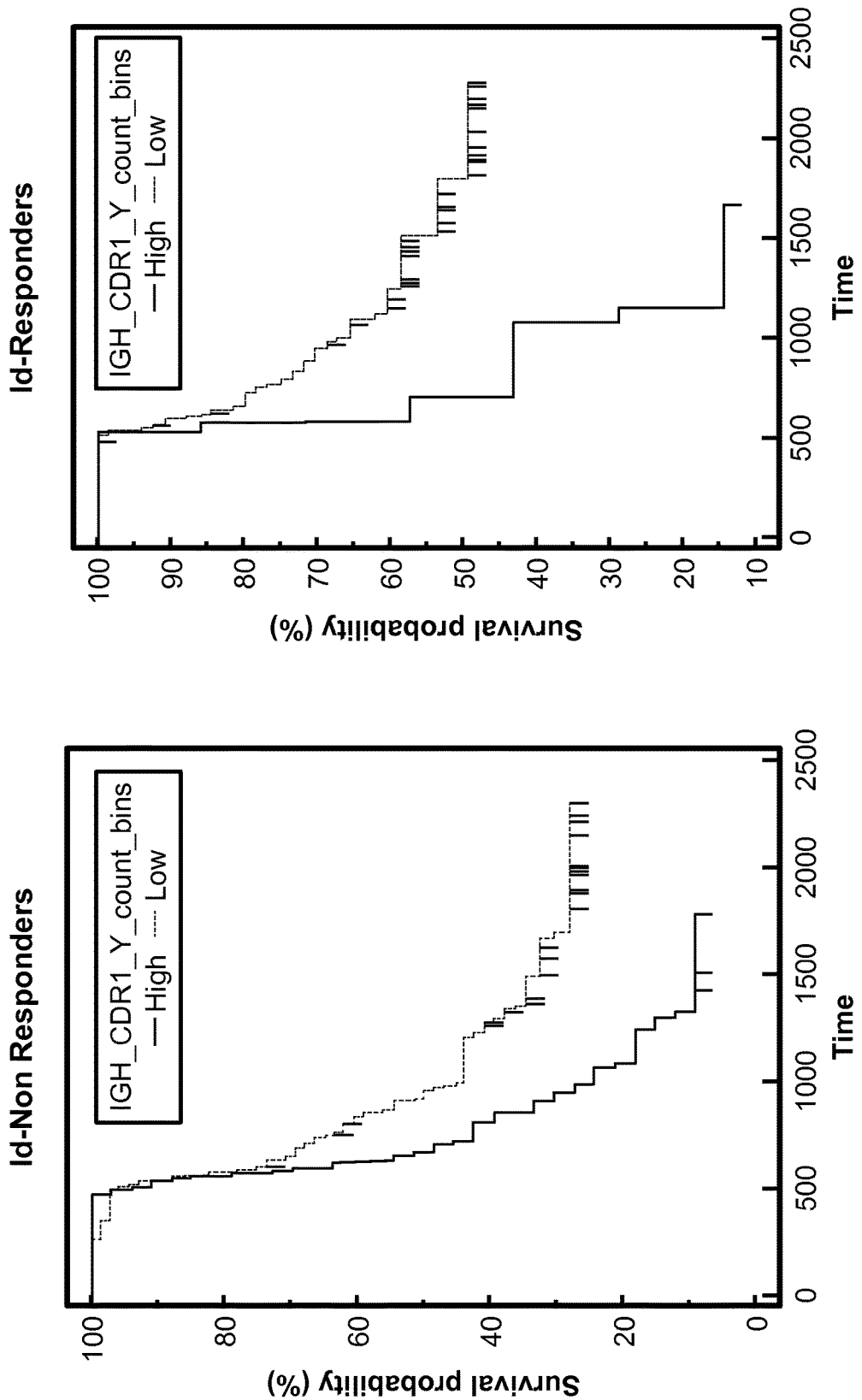
FIG. 8: Tyrosine frequency in CDR1 is independent of anti-Id humoral immune response as a predictor of PFS among patients receiving MyVax. Kaplan-Meier curves depict patients stratified by CDR1 tyrosine count (CDR1-Yhi from CDR1-Ylo as defined in FIG. 6), with the log-rank test used to test significance of separation (XX) among patients with robust anti-iditotype humoral responses (Id-Responders, right panel), or those failing to mount such immune responses (Id-Non Responders, left panel). X-axis represents time from registration, and Y-axis represents Progression Free Survival.

The CDR H1+L Y-count has ability not only to predict immune response, but also to independently predict progression free survival (PFS). Even among the Id-R and Id-NR subgroups, the number of tyrosines in CDR H1/L1 predicts PFS (FIG. 8).

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, medicine, and molecular biology or related fields are intended to be within the scope of the following claims.

What is claimed is:

1. A method for administering a vaccine to a patient suffering from an immunoglobulin positive (Ig+) B lineage malignancy, the method comprising:
   obtaining a biological sample from a patient suspected of having an Ig+B lineage malignancy, which biological sample comprises tumor cells;
   detecting three of fewer tyrosine residues in one or both of the Ig heavy and Ig light chain CDR1 regions in the biological sample; and
   administering a vaccine comprising said tumor specific idiotype to the patient.

2. The method of claim 1 wherein the biological sample is selected from biopsy of an enlarged lymph node (LN) or other extranodal tissue involved by lymphoma; fine needle aspiration of an enlarged LN; blood; and bone marrow aspiration.

3. The method of claim 1, wherein the immunoglobulin positive (Ig+) B lineage malignancy is a non-Hodgkin lymphoma (NHL).

4. The method of claim 3, wherein the NHL is a follicular lymphoma.

* * * * *